(12) United States Patent
Messersmith et al.

(10) Patent No.: US 10,676,509 B2
(45) Date of Patent: Jun. 9, 2020

(54) SURFACE-IMMOBILIZED ANTIMICROBIAL PEPTOIDS

(75) Inventors: Phillip B. Messersmith, Clarendon Hills, IL (US); Annelise E. Barron, Palo Alto, CA (US); Andrea Statz, Flagstaff, AZ (US); Nathaniel Chongslriwatana, Albuquerque, NM (US)

(73) Assignee: Northwestern University, Evanston, IL (US)

( * ) Notice: Subject to any disclaimer, the term of this patent is extended or adjusted under 35 U.S.C. 154(b) by 2724 days.

(21) Appl. No.: 12/533,876

(22) Filed: Jul. 31, 2009

(65) Prior Publication Data

US 2010/0028719 A1    Feb. 4, 2010

Related U.S. Application Data

(60) Provisional application No. 61/137,482, filed on Jul. 31, 2008.

(51) Int. Cl.

| | |
|---|---|
| *C07K 7/08* | (2006.01) |
| *C09D 5/14* | (2006.01) |
| *B08B 17/06* | (2006.01) |
| *C07K 14/00* | (2006.01) |
| *C07K 7/06* | (2006.01) |
| *C09D 5/16* | (2006.01) |

(52) U.S. Cl.
CPC ............... *C07K 7/08* (2013.01); *B08B 17/06* (2013.01); *C07K 7/06* (2013.01); *C07K 14/001* (2013.01); *C09D 5/14* (2013.01); *C09D 5/1637* (2013.01)

(58) Field of Classification Search
None
See application file for complete search history.

(56) References Cited

U.S. PATENT DOCUMENTS

| | | | | |
|---|---|---|---|---|
| 7,618,937 | B2 * | 11/2009 | Messersmith et al. ........ | 514/1.1 |
| 8,445,632 | B2 * | 5/2013 | Barron ................. | C07K 5/0815 |
| | | | | 530/300 |
| 2006/0241281 | A1 * | 10/2006 | Messersmith et al. ........ | 530/324 |
| 2008/0171012 | A1 * | 7/2008 | Messersmith et al. .... | 424/78.09 |
| 2010/0028719 | A1 * | 2/2010 | Messersmith et al. ........ | 428/702 |
| 2010/0330025 | A1 * | 12/2010 | Messersmith et al. .... | 424/78.17 |

FOREIGN PATENT DOCUMENTS

WO    WO 2006/055531    *   5/2006

OTHER PUBLICATIONS

Hooks et al. Development of homomultimers and heteromultimers of lung cancer-specific peptoids. Biopolymers. 2011;96(5):567-77. PubMed PMID: 22180904. Full Text Available @: http://onlinelibrary.wiley.com/doi/10.1002/bip.21596/pdf.*
Statz et al. Surface-immobilized antimicrobial peptoids. Biofouling. Aug. 27, 2008 (Entered STN); 24(6): 439-448. https://www.ncbi.nlm.nih.gov/pmc/articles/PMC2654338/pdf/nihms-99255.pdf.*
Chongsiriwantana et al. Peptoids that mimic the structure, function, and mechanism of helical antimicrobial peptides. PNAS; Feb. 26, 2008, vol. 105, No. 8, 2794-2799.*
Statz et al. Protein, cell and bacterial fouling resistance of polypeptoid-modified surfaces: effect of side-chain chemistry. Soft Matter (2008), 4(1), 131-139, first published online Oct. 12, 2007; https://pubs.rsc.org/en/content/articlepdf/2008/sm/b711944e.*
Chongsiriwantana, NP; Patch, JA; Czyewski, AM; Dohm, MT; Ivankin, A; Gidalevitz, D; Zuckerman, R; Barron, AE. Peptoids that mimic the structure, function, and mechanism of helical antimicrobial peptides. PNAS Feb. 26, 2008, vol. 105, No. 8, 2794-2799.
Patch, JA; Barron, AE. Helical Peptoid Mimics of Magainin-2 Amide. J. Am. Chem. Soc. 2003, 125, 12092-12093.
Statz, AR; Kuang, J; Ren, C; Barron, AE; Szleifer, I; Messersmith, PB. Experimental and theoretical investigation of chain length and surface coverage on fouling of surface grafted polypeptoids. Biointerphases 4(2), Jun. 2009, FA22-32.
Statz, AR; Park, JP; Chongsiriwatana, NP; Barron, AE; Messersmith, PB. Surface-immobilised antimicrobial peptoids. Biofouling. 2008; 24(6): 439-448. DOI: 10.1080/08927010802331829.

* cited by examiner

*Primary Examiner* — Maury A Audet
(74) *Attorney, Agent, or Firm* — Quarles & Brady LLP

(57) ABSTRACT

Immobilizable antimicrobial compounds incorporating antimicrobial and/or antifouling components, as can be adhered to various device structures and components.

13 Claims, 12 Drawing Sheets

PMP1-AMP
  H-NLys-Nspe-Nspe-NLys-Nspe-L-Pro-(NLys-Nspe-Nspe)$_2$-(Nme)$_{20}$-Ntfe-(DOPA-Lys)$_2$-DOPA-NH$_2$ PMP1-C
  H-(NLys-Nssb-Nssb)$_4$-(Nme)$_{20}$-Ntfe-(DOPA-Lys)$_2$-DOPA-NH$_2$ PMP1$_{10}$
  H-(Nme)$_{10}$-(DOPA-Lys)$_2$-DOPA-NH$_2$

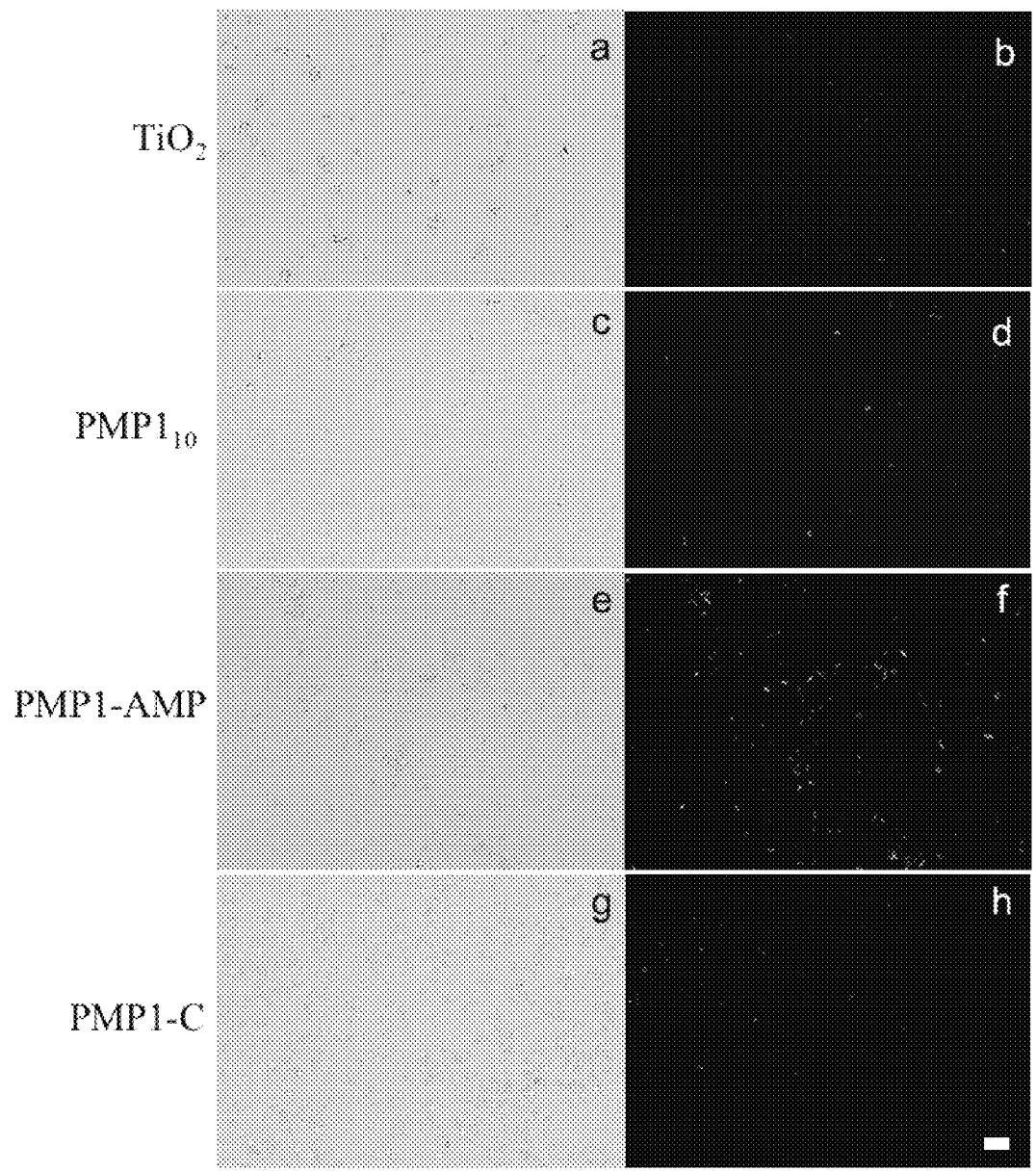
Figures 3A-H

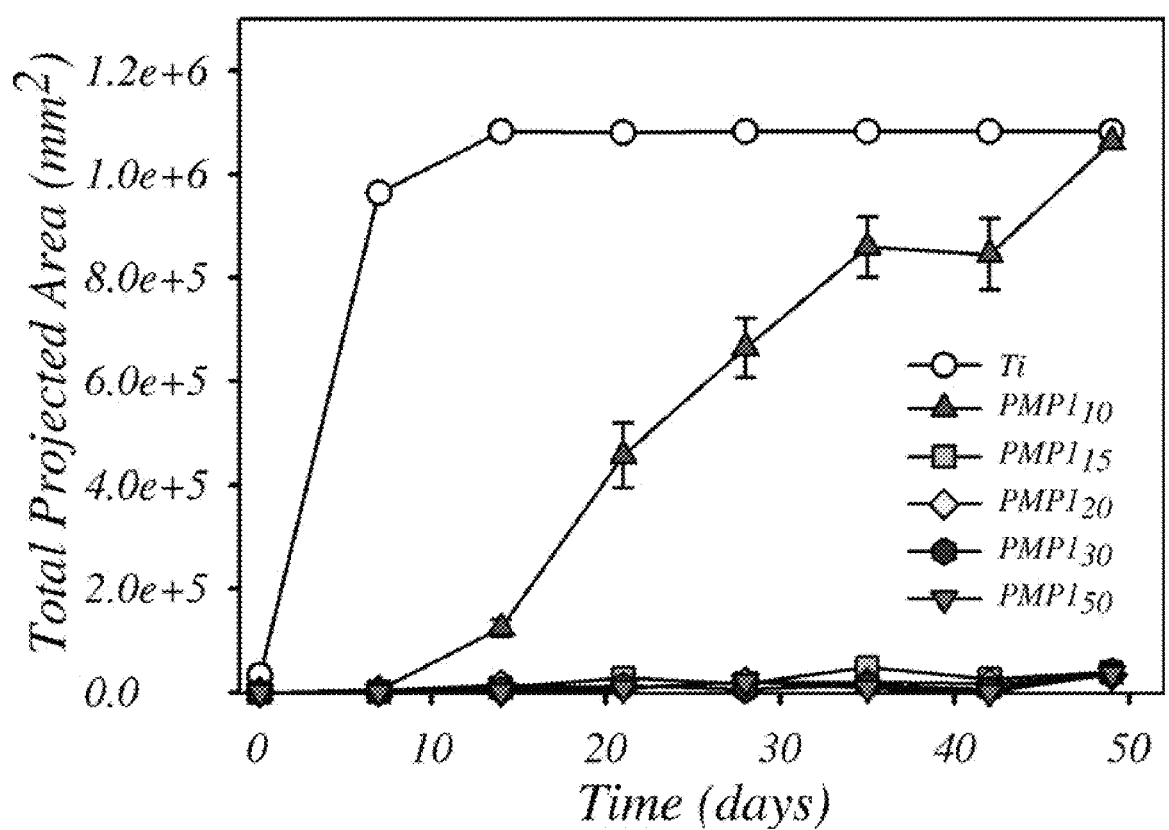

SURFACE-IMMOBILIZED ANTIMICROBIAL PEPTOIDS

This application claims priority to provisional application Ser. No. 61/137,482 filed Jul. 31, 2008, which is incorporated herein by reference in its entirety.

The United States government has certain rights to this invention pursuant to grant no. DE 14192 from the National Institutes of Health to Northwestern University.

BACKGROUND OF THE INVENTION

Potential applications of surface-immobilized antimicrobial polymers include, for example, as coatings on medical devices, water purification systems, food packaging, and hospital equipment. Bacterial infections on implanted medical devices such as catheters and pacemakers can lead to serious complications and often, to device removal, because the adherent bacterial can form a biofilm, which provides a protective environment for bacteria, allowing them to resist killing by antibiotics, as well as immune responses.

Strategies to limit bacterial fouling of surfaces can incorporate either passive or active elements. Passive approaches to fouling prevention lack an active antibacterial component and typically involve the use of antifouling polymer surface coatings to provide steric resistance to physical attachment of bacteria. Examples of polymers and/or polymeric components that have been shown to reduce short-term bacterial attachment include poly(ethylene glycol) (PEG), self-assembled monolayers (SAMs), and peptidomimetic polymers.

Surface coatings may also contain active components capable of killing bacteria through direct contact or via a leachable compound. Examples of active antibacterial coatings include cationic polymers such as chitosan and polymers containing quaternary ammonium and pyridinium functional groups. The antibacterial effect of silver can be exploited by incorporation of silver salts or silver nanoparticles into coatings. Another reported approach for creating antibacterial surfaces involves the direct attachment of antibiotics such as vancomycin and penicillin to surfaces. Alternatively, antimicrobial peptides (AMPs) offer activity against a wide range of organisms, while functioning with some selectivity for bacteria over mammalian cells, and there have been recent reports of AMP imobilization on surfaces.

Several non-natural mimics of antimicrobial peptides with high activity have recently been developed, providing advantages in terms of chemical diversity and significant resistance to protease degradation. For example, the linear cationic α-helical class of AMPs has been successfully mimicked as β-peptides and as poly-N-substituted glycines (peptoids). Peptoids are non-natural mimics of polypeptides with their side chains appended to the amide nitrogen instead of to the α-carbon. Peptoids are well suited for antibacterial peptide use because they have been shown to be resistant to proteolytic enzymes; the well-known submonomer synthesis method of Zuckermann et al. allows for great versatility of the side-chain chemistry; and conformationally stable helical secondary structures can be formed by incorporating sterically bulky, α-chiral side chains. Peptoid mimics of antimicrobial peptides (ampetoids) with helical structures that exhibit antibacterial activity in solution have been synthesized previously. (See, Patch J A, Barron A E (2003) Helical Peptoid Mimics of Magainin-2 Amide. *Journal of the American Chemical Society*, 125, 12092-12093; and Chongsiriwatana N P, Patch J A, Czyzewski A M, Dohm M T, Ivankin A, Gidalevitz D, Zuckermann R N, Barron A E (2008) Peptoids that mimic the structure, function, and mechanism of helical antimicrobial peptides. *Proceedings of the National Academy of Science USA*, 105, 2794-2799, each of which is incorporated herein by reference in its entirety.) Several ampetoids were recently tested for broad-spectrum activity against bacteria, as well as for cytotoxicity against various mammalian cells, revealing certain sequence-specific oligopeptoids that have antibacterial activities equivalent to or better than cationic antimicrobial peptides and with strong selectivity for killing bacteria over mammalian cells; and co-pending application Ser. No. 12/378,034 filed Feb. 9, 2009, also incorporated herein by reference in its entirety.

Certain peptoids, with different sequences and chain lengths, can also offer passive resistance to biofouling much like other antifouling polymers, as was first established with surfaces coated with a linear poly(N-methoxyethyl glycine), or pNMEG peptoid. (See, co-pending application Ser. No. 11/280,107, filed Nov. 16, 2005, the entirety of which is incorporated herein by reference.) Protein and cell adhesion onto $TiO_2$ was dramatically reduced by coating with this peptoid, which has side-chains similar to the repeat unit of polyethylene glycol (PEG). A follow-up study revealed a dramatic reduction in *Staphylococcus epidermidis* and *Escherichia coli* bacterial adhesion when compared to unmodified $TiO_2$ substrates, presumably due to the pNMEG peptoid's passive inhibition of bacterial cell attachment by virtue of its unique chemical structure.

SUMMARY OF THE INVENTION

In light of the foregoing, it is an object of the present invention to provide new poly-N-substituted glycine compounds and methods for, and/or therapies, that relate to their use as antibiotics, thereby improving upon the prior art and/or overcoming various deficiencies or shortcomings thereof. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide such compounds having minimum inhibitory concentrations in the low micromolar range and showing activity against both Gram-positive and Gram-negative bacteria, with lower mammalian cytotoxicities and negligible hemolysis, at such concentrations, as compared to compounds of the prior art.

It can be another object of the present invention to provide such compounds, an ampetoid component thereof variable by residue sequence and/or N-substituent, so as to affect its hydrophobicity and/or amphipathicity, and hence to affect its mechanism of action, and/or to enhance its selectivity for killing bacteria rather than mammalian cells.

It can be another object of the present invention to provide a new class of N-alkylated peptoids, providing such potencies and selectivities at monomer numbers and peptoid lengths shorter than previously available.

It can be another object of the present invention, alone or in conjunction with one or more of the preceding objectives, to provide such ampetoid components in combination with a passive polypeptoid anti-fouling component and/or such an anti-fouling compound.

It can be another object of the present invention to provide such compound(s) as a coating on, coupled or otherwise adhered to an article of manufacture, such compound(s) affording both anti-microbial activity and anti-fouling effect. This coating can either remain unchanged over time, or alternatively, could provide for a slow, controlled release of the initially tethered peptoids, providing different ways of eliminating pathogenic bacteria and their colonies, as opposed to direct killing by surface-bound molecules.

Other objects, features, benefits and advantages of the present invention will be apparent from this summary and its descriptions of certain embodiments, and will be readily apparent to those skilled in the art having knowledge of various peptidomimetic compounds and their syntheses, chemical modification, and uses. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to an antimicrobial compound. Such a compound can comprise an ampetoid component comprising 2- about 18 monomeric residues, each said residue as can be independently selected from proline residues and N-substituted glycine residues, with such N-substituents as can be independently selected from about $C_4$- about $C_{20}$ linear, branched and cyclic alkyl moieties, α-amino acid side chain moieties and carbon homologs thereof, providing such a component is amphiphatic and has a net positive charge under physiological conditions. Such an ampetoid component can be coupled to an anchor component comprising at least one N- or α-substituted glycine residue, each such substituent comprising a moiety selected from a dihydroxyphenyl moiety and an amine-terminated $C_1$- about $C_{10}$ alkyl moiety.

In certain embodiments, such an ampetoid component can be of a formula

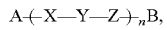

where A can be selected from H and a terminal N-alkyl substituted glycine residue, where such an alkyl substituent can be selected from about $C_4$ to about $C_{20}$ linear, branched and cyclic alkyl moieties; n can be an integer selected from 1-3; B can be selected from a covalent bond, and 1-3 N-substituted glycine residues, such N-substituents as can be independently selected from α-amino acid side chain moieties and structural/functional analogs thereof; and X, Y and Z can also be independently selected from N-substituted glycine residues, such N-substituents as can be independently selected from α-amino acid side chain moieties and structural/functional analogs thereof and proline residues. As described elsewhere herein and/or in the incorporated co-pending '034 application, such X—Y—Z periodicity can provide such a component a certain amphipathicity. As would be understood by those skilled in the art made aware of this invention, such structural and/or functional analogy can be considered in the context of any such α-amino acid side chain, N-substituent and/or a sequence of such N-substituted glycine residues, such structure and/or function including but not limited to charge, chirality, hydrophobicity, amphipathicity, helical structure and facial organization. Such analogs include, without limitation, carbon homologs of such side chain—such homologs as would be understood in the art as including but not limited to plus or minus 1 or 2 or more methylene and/or methyl groups.

Regardless, in certain embodiments A can be H, and B can be selected from one or two N-substituted glycine residues, such a selection as can reduce the hydrophobicity of such a component, as compared to components of 3-fold periodicity. In certain such embodiments, X can be an $N_{Lys}$ residue; n can be 2-3; and B can be two N-substituted glycine residues. Without limitation, such a component can be of a formula

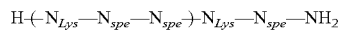

In various other embodiments, regardless of identity of A, X and B, at least one of Y and Z can be a proline residue. In certain such embodiments, X, Y and Z can be proline residues.

In certain other embodiments, A can be a terminal N-alkyl substituted glycine residue, with such an alkyl substituent as can be selected from about $C_6$ to about $C_{18}$ linear alkyl moieties. Regardless, B can be a covalent bond, and n can be selected from 1 and 2. In certain such embodiments, A can be a terminal N-alkyl substituted glycine residue, with an alkyl substituent selected from about $C_6$ to about $C_{18}$ linear alkyl moieties. Regardless, B can be an $N_{Lys}$ residue, and n can be 1.

In certain other non-limiting embodiments, such an ampetoid component can be of a formula

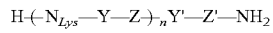

wherein n can be selected from 2 and 3; and Y, Z, Y' and Z' can be independently selected from N-substituted glycine residues, where such substituents can be independently selected from α-amino acid side chain moieties and carbon homologs thereof. Such Y' and Z' residues can be selected to provide such a component reduced hydrophobicity as compared to a component of 3-fold periodicity. In certain such embodiments, at least one of X and Y can be a proline residue. Regardless, n can be selected from 2 and 3, and Y' can be an $N_{Lys}$ residue. In certain such embodiments, one or both X and Y can be proline residues. Without limitation, such a component with reduced hydrophobicity can be of a formula

In yet other embodiments, such an ampetoid component can be of a formula

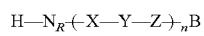

wherein B can be selected from a covalent bond and X'; X, Y, Z and X' can be independently selected from N-substituted glycine residues, where such substituents can be independently selected from α-amino acid side chain moieties and carbon homologs thereof; n can be an integer selected from 1 and 2; N can be a glycine residue; and R can be an N-alkyl substituent of such a glycine residue, as can be selected from about $C_4$ to about $C_{20}$ linear, branched and cyclic alkyl moieties. In certain embodiments, n can be 2, and B can be a covalent bond. In certain other embodiments, n can be 1, and B can be X'. Accordingly, one or both of X and X' can be $N_{Lys}$ residues. Regardless, an alkyl substituent can be selected from about $C_6$ to about $C_{18}$ linear, branched and cyclic alkyl moieties, and X and X' can be $N_{Lys}$ residues. Without limitation, such a component can be of a formula

In yet other non-limiting embodiments, such an ampetoid component can comprise an N-terminus selected from H and an N-alkyl substituted glycine residue, where such an alkyl substituent can be selected from about $C_4$ to about $C_{20}$ linear, branched and cyclic alkyl moieties; a C-terminus selected from a covalent bond, one and two N-substituted glycine residues, such N-substituents as can be independently selected from α-amino acid side chain moieties and structural/functional analogs thereof, and 2 to about 15 monomeric residues between the N- and C-termini, each such residue as can be independently selected from proline residues and N-substituted glycine residues, such N-substituents as can be independently selected from α-amino acid side chain moieties and structural/functional analogs thereof.

As illustrated herein and/or the aforementioned '034 application and as distinguished over the prior art, such monomers can be selected to provide such a component a non-periodic sequence of monomers. As would be understood by those skilled in the art made aware of this invention, such structural and/or functional analogy can be considered in the context of any such α-amino acid side chain, N-substituent and/or a sequence of such N-substituted glycine residues, such structure and/or function including but not limited to charge, chirality, hydrophobicity, amphipathicity, helical structure and facial organization. Such analogs include, without limitation, carbon homologs of such side chain—such homologs as would be understood by those skilled in the art, including but not limited to plus or minus 1 or 2 or more methylene and/or methyl groups.

In certain such embodiments, the N-terminus of such a component can be H; and the C-terminus can be selected from said one and two N-substituted glycine residues. Regardless, such a component can comprise 1 to about 5 (X—Y—Z) non-periodic trimers. In certain such embodiments, at least one of X, Y and Z in each of the trimers can be selected to interrupt 3-fold periodicity. Without limitation, at least one X in at least one said trimer can be an $N_{Lys}$ residue. In certain such embodiments, at least one of Y and Z in at least one such trimer can be a proline residue. In various other non-limiting embodiments, the monomeric residues can comprise at least two non-consecutive of the same or repeat trimers, with at least one such residue therebetween to interrupt periodicity. In certain such embodiments, at least one X in at least one such trimer can be an $N_{Lys}$ residue, and at least one of Y and Z in at least one said trimer can be a proline residue. Without limitation, one such component can be as designated AMP, below and as illustrated in FIG. 1.

In various other non-limiting embodiments, the N-terminus of such a component can be an N-alkyl substituted glycine residue, with an alkyl substituent as can be selected from about $C_6$ to about $C_{18}$ linear alkyl moieties. Regardless, such a component can comprise 1 to about 5 (X—Y—Z) non-periodic trimers. In certain such embodiments, at least one of X, Y and Z in each of the trimers can be selected to interrupt 3-fold periodicity. In certain other embodiments, the monomeric residues can comprise at least two non-consecutive of the same or repeat trimers, with at least one residue therebetween to interrupt peridicity. In certain such embodiments, at least one X in at least one said trimer can be an $N_{Lys}$ residue, and at least one of Y and Z in at least one said trimer can be a proline residue.

Regardless of identity, such an ampetoid component can be coupled to an anchor component comprising at least one N- or α-substituted glycine residue, such a substituent as can comprise a moiety selected from dihydroxyphenyl moieties and amine-terminated $C_1$- about $C_{10}$ alkyl moieties. In certain non-limiting embodiments, such an anchor component can comprise at least one residue, whether N- or α-substituted, comprising a dihydroxyphenyl moiety, such a residue alone or in combination with one or more other residues, whether N- or α-substituted, comprising an amine-terminated alkyl moiety. In certain such embodiments, such an anchor component can be selected from components comprising at least two residues comprising a substituent comprising a dihydroxyphenyl moiety (e.g., without limitation, a DOPA moiety), and/or at least two residues comprising an amine-terminated alkyl moiety (e.g., without limitation, a lysine moiety). Without limitation, various anchor components useful in conjunction with the antimicrobial compounds of this invention are described in the aforementioned co-pending '107 application.

Regardless of either ampetoid or anchor component identity, such an antimicrobial compound can comprise an anti-fouling component comprising at least one N-alkoxyalkyl substituted glycine residue. In certain such embodiments, such an anti-fouling component can couple ampetoid and anchor components. Without limitation, an anti-fouling component can comprise about 5- about 50 such glycine residues. Regardless, one or more of such residues can comprise an N-fomethoxyethyl substituent. In certain such embodiments, such an anti-fouling component can comprise about 10- about 25 such residues. Various non-limiting anti-fouling components are as illustrated elsewhere herein or described in the aforementioned co-pending '107 application.

In part, the present invention can also be directed to one or more antimicrobial peptoid compositions comprising one or more of the poly-N-substituted glycine compounds of this invention. Such compounds can optionally comprise one or more antimicrobial peptides and/or one or more antimicrobial or anti-fouling peptidomimetic compounds now or hereafter known in the art. Accordingly, this invention can be directed to a range of compositions comprising one or more of the present polypeptoid/ampetoid compounds, optionally with an antimicrobial component of the prior art. Such compositions can be prepared, assembled, and/or employed as would be understood by those skilled in the art made aware of this invention.

Regardless, as illustrated below, any of the present antimicrobial compounds and/or related compositions can be used alone or in combination with one or more anti-fouling compounds in conjunction with an article of manufacture to compromise, inhibit and/or otherwise deter bacterial growth thereon or adversely affect, inhibit and/or prevent attachment of bacteria thereto. Without limitation, such antimicrobial and/or anti-fouling compounds can be coupled to or conjugated with a metal substrate of such an article. In certain embodiments, such a substrate can comprise a metal oxide, including but not limited to titanium oxide. Without limitation, such substrates can be present in conjunction with various medical, biomedical and therapeutic articles and devices, such articles, devices as would be known to those skilled in the art made aware of this invention. Without limitation, such devices and corresponding metal substrates include those described in the aforementioned co-pending '107 application.

In one non-limiting respect, the passive resistance of N-methoxyethyl glycine peptoids can be combined with an active antibacterial peptoid sequence. Corresponding results demonstrate a reduction in protein adsorption and fibroblast cell attachment. For surfaces incorporating an antibacterial peptoid sequence, a large fraction of attached bacteria with compromised membranes, can indicate that such immobilized antibacterial peptoid remains active. Accordingly, without limitation, this invention can be directed to surfaces and related techniques capable of killing adherent bacteria, as can provide solutions to infections associated with implantable medical devices. For instance, antimicrobial peptoid oligomers (ampetoids) can be designed to mimic helical antimicrobial peptides, such ampetoids as can be synthesized with a peptoid spacer chain to allow mobility, and an adhesive peptide moiety for easy and robust immobilization onto a substrate. In certain non-limiting embodiments, TiO$_2$ substrates can be modified with such ampetoids and subsequently backfilled with an antifouling polypeptoid polymer in order to create polymer surface coatings composed of both antimicrobial (active) and antifouling (passive) peptoid functionalities. Demonstrating but one utility of this invention, confocal microscopy images show that the membranes of adherent E. coli were damaged after 2 h exposure to such modified substrates, and had lost their natural barrier function—showing that ampetoids of this invention retain antimicrobial properties when immobilized onto a substrate.

BRIEF DESCRIPTION OF THE DRAWINGS

FIG. 3: Confocal microscopy images (phase contrast images on left and fluorescent images on right) for E. coli after 2 h incubation on: bare TiO$_2$ (A and B), PMP1$_{10}$ (c and d), PMP1-AMP (e and f), and PMP1-C (g and h) modified substrates. Scale bar=10 µm.

FIG. 12: Total projected area of 3T3 fibroblasts during long-term cell culture on unmodified TiO$_2$, Tyr-PMP1$_{10+}$ and PMP1$_n$ modified TiO$_2$ substrates.

DETAILED DESCRIPTION OF CERTAIN EMBODIMENTS

Figure 1:
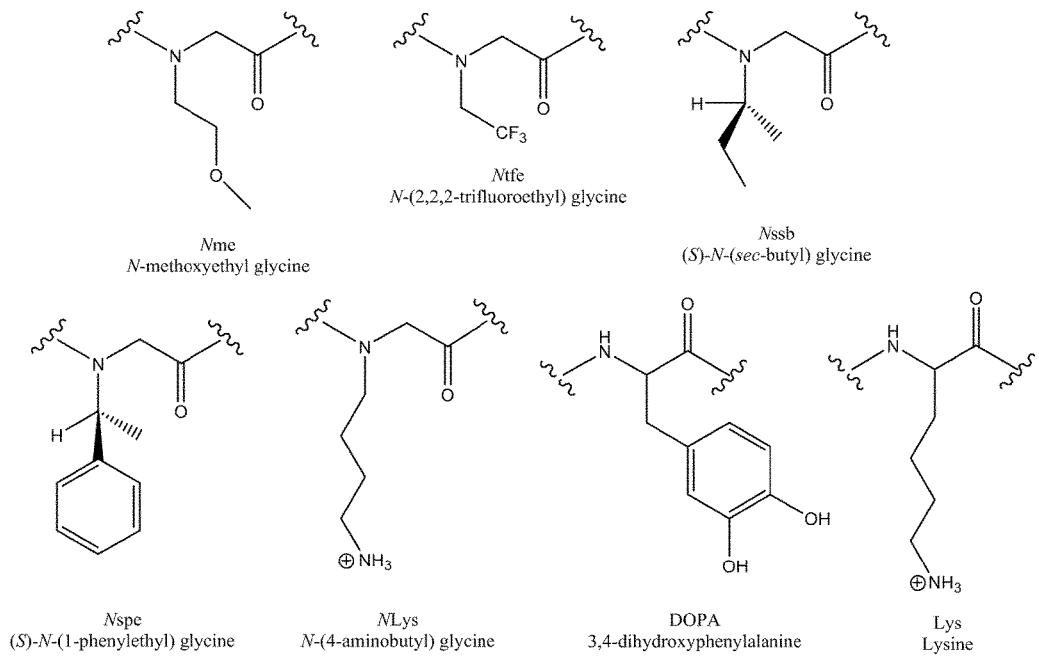
FIG. 1: Representative polymer sequences, peptoid residue monomer structures and amino acid residue structures, with abbreviations, in accordance with various non-limiting embodiments of this invention.

The antimicrobial peptoids of this invention incorporate previously identified sequences that mimic helical antimicrobial peptides (See, Patch & Barron; Chongsiriwatana et al., supra). With reference to FIG. 1, PMP1-AMPs contain an n-terminal 12-mer peptoid sequence comprising α-chiral aromatic (S)—N-(1-phenylethyl)glycine (Nspe), achiral cationic N-(4-aminobutyl)glycine (NLys) and proline residues, selected based on its reported low MIC and high selectivity ratio for bacterial cells over mammalian cells (Chongsiriwatana et al., supra). PMP1-C contains a terminal 12-mer peptoid sequence comprising bulky α-chiral side-chains (S)—N-(sec-butyl)glycine (Nssb) and cationic N-(4-aminobutyl)glycine (NLys) residues, and was selected as a control because this sequence exhibited very low antibacterial and hemolytic activity (Patch & Barron, supra). Both polymers were tethered to the substrate surface via a peptide/peptoid construct composed of adhesive peptides (DOPA, Lys) and antifouling peptoids (Nme). The (Nme)$_{20}$-(DOPA-Lys)$_2$-DOPA construct (PMP1) was previously shown to adsorb strongly to TiO$_2$ substrates and provide excellent protein and cell fouling-resistant properties (See, e.g. the aforementioned co-pending '107 application). A shorter version of this construct, PMP1$_{10}$, was synthesized in order to 'backfill' the surfaces with a passive antifouling peptoid after modification with PMP1-AMP. The polymers were purified using RP-HPLC, and the purity and molecular weight of the resulting fractions were determined using RP-HPLC and MALDI-MS.

The polymers were initially tested to determine their antibacterial properties in the solution state. Antibacterial activities of the compounds were tested using the methods described above for both Gram-negative and Gram-positive bacterial strains. The minimum inhibitory concentrations (MICs) are reported in Table 1. While PMP1-AMP was active against all bacterial strains, the MIC was 2-4 times greater than that for AMP alone; this increase can likely be explained by the presence of the additional 26 residues contained in the Nme tether and adhesive anchor portion of the polymer. As expected, peptoid C, PMP1-C and PMP1$_{10}$ were not active at the tested concentrations. While MIC values are useful predictors for antimicrobials in solution, these measurements do not directly correlate to the amount required for surface-immobilized applications because interactions between the bacteria and the immobilized polypeptoids are expected to differ from the interactions when the ampetoids are free in solution.

TABLE 1

Antibacterial activities (MICs) of the ampetoids and polymer components with E. coli, B. subtilis, S. epidermidis, and P. aeruginosa.

| | MIC (uM) | | | |
| --- | --- | --- | --- | --- |
| | E. coli | B. subtilis | S. epidermidis | P. aeruginosa |
| PMP1-AMP | 50 | 3.1 | 3.1 | 200 |
| AMP | 12.5 | 1.6 | 1.6 | 25 |
| PMP1-C | >100 | >100 | >100 | >100 |
| Peptoid C | >100 | >100 | >100 | >100 |
| PMP1 | >100 | >100 | >100 | >100 |

The effects of the additional peptide and peptoid residues on the secondary structure of AMP were investigated by measuring the overall helix structure of the polymers using circular dichroism (CD) spectroscopy. PMP1-AMP and AMP exhibited similar spectral features, indicating the presence of a defined helical structure as was shown previously for AMP (Chongsiriwatana et al., supra). The helical structures of PMP1-AMP and AMP are believed due to the incorporation of bulky α-chiral side chains which cause steric constraints. Peptoid C, PMP1-C and PMP1$_{10}$ did not have helical structures.

Adsorption of the polymers onto TiO$_2$ substrates was investigated using OWLS and XPS. In order to create surfaces with both active antibacterial and passive antifouling properties, surfaces were modified with PMP1-AMP or PMP1-C first and then backfilled with the shorter PMP1$_{10}$. Modifying surfaces with a two-step approach involving grafting of a longer polymer followed by backfilling with a shorter one, has been shown to be an effective strategy for enhancing antifouling performance of polymer brushes. In the present case, for example, backfilling with PMP1$_{10}$ was believed to facilitate extension of the active AMP moiety away from the surface for interaction with bacteria that encounter the modified surface. Like antimicrobial peptides, ampetoids should interact with the bacterial membranes and mobility of the longer ampetoid chains should enhance antibacterial activity. For instance, it has been demonstrated that poly(ethylene glycol) spacers were necessary when immobilizing cathelin LL37 on titanium surfaces because lateral mobility of surface-bound AMPs and parallel orientation of the peptide helices are required for interaction of the peptides with bacterial membranes.

Figure 2A:
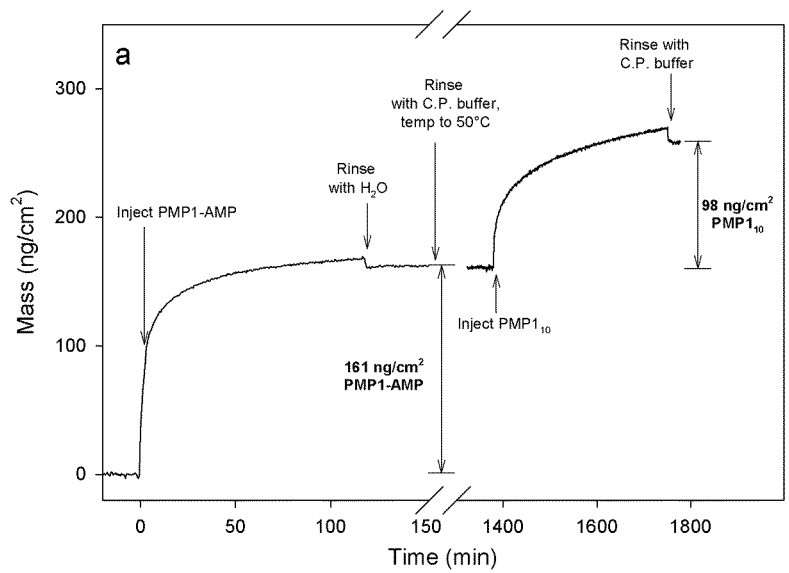
FIG. 2: OWLS plot of mass adsorption for PMP1-AMP and PMP1$_{10}$ (A) and PMP1-C and PMP1$_{10}$ (B).
Figure 2B:
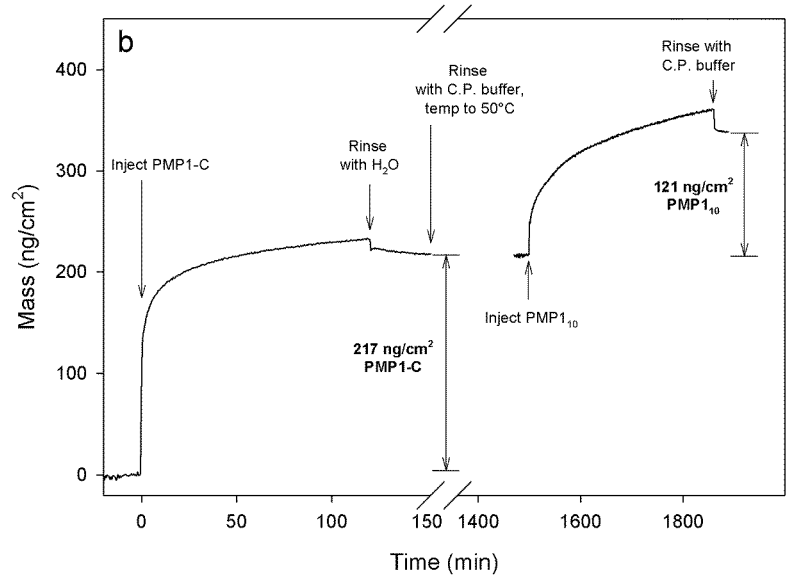

Optimum modification conditions were determined by conducting OWLS experiments; PMP1-AMP was adsorbed onto TiO$_2$ waveguides using various concentrations and modification conditions. The goal was to adsorb a sub-monolayer coating of the polymer onto the surface. Subsequently, PMP1$_{10}$ was adsorbed on the waveguide containing the PMP1-AMP layer in order to backfill between the ampetoid chains with this antifouling polymer. While the PMP1$_{10}$ may be able to adsorb on top of the PMP1-AMP layer, it was believed that the PMP1$_{10}$ will adsorb to any remaining exposed areas of the TiO$_2$ waveguide due to the strong interactive forces between DOPA residue(s) and metal oxides. The OWLS mass plot, shown in FIG. 2A, represents the optimum conditions for two-stage adsorption: 2 h adsorption of a 0.5 mg/ml solution of PMP1-AMP in H$_2$O, followed by 6 h adsorption of a 1.0 mg/mil solution of PMP1$_{10}$ in C.P. buffer. The resulting adsorbed masses correlate to a polymer coating composed of approximately 40% PMP1-AMP antibacterial polymer and 60% of PMP1$_{10}$ antifouling polymer. The experiments were repeated using identical adsorption conditions for PMP1-C, shown in FIG. 2B, yielding a surface composed of approximately 43% antibacterial polymer and 57% antifouling polymer. These conditions were selected for preparation of mixed surfaces in all subsequent experiments.

The elemental compositions of the polymer layers are reported in Table 2, derived from XPS survey scan spectra (not shown). C, N and O signals are representative of the peptide/peptoid backbone and side-chains of the polymers. Ti signal was detected for all samples from the underlying TiO$_2$ substrates. The decrease in Ti signal for PMP1$_{10}$-modified substrates indicates successful modification, and the further decrease in Ti % for the PMP1-AMP and PMP1-C surfaces backfilled with PMP1$_{10}$ suggests that the polymer coating becomes thicker during the backfilling step. The detected F signal is from the single trifluoroethyl glycine residue included in the PMP1-AMP and PMP1-C polymers; the presence of the F signal after backfilling indicates that PMP1-AMP and PMP1-C remained on the surface after backfilling with PMP1$_{10}$.

TABLE 2

Atomic compositions of bare and modified TiO$_2$ substrates as determined from high-resolution XPS spectra.

| Substrates | Experimental Composition (atom %) | | | | |
|---|---|---|---|---|---|
|  | C | N | O | F | Ti |
| TiO$_2$ | 16.8 | 0.2 | 54.8 | 0.0 | 28.2 |
| PMP1$_{10}$ only | 48.5 | 6.9 | 34.8 | 0.0 | 9.8 |
| PMP1-AMP* | 54.1 | 8.3 | 29.5 | 0.2 | 7.9 |
| PMP1-C* | 52.8 | 7.3 | 32.0 | 0.2 | 7.7 |

*back-filled with PMP110

Bacterial experiments on modified TiO$_2$ slides were performed by exposing the surfaces to an *E. coli* suspension for two hours and then centrifuging to remove unattached and weakly attached bacteria. The bacteria remaining on the surfaces were imaged in phase contrast for determination of cell numbers, and in fluorescence after staining with FITC to detect cells with compromised membranes. Images of representative areas of the substrates are shown in FIG. 3. From these images, total number of adherent bacteria (from phase contrast) and percent of attached cells with compromised membranes (from FITC staining) were determined and are shown in Table 3.

TABLE 3

Quantification of bacterial adhesion and membrane permeation on bare and modified TiO$_2$ substrates. Standard deviations from the mean for nine images are reported.

| Substrates | Total Cell Count (cells/cm$^2$) | % FITC-stained |
|---|---|---|
| TiO$_2$ | 74 ± 31 | 5 ± 3 |
| PMP1$_{10}$ only | 20 ± 7 | 27 ± 15 |
| PMP1-AMP* | 87 ± 13 | 69 ± 25 |
| PMP1-C* | 189 ± 82 | 4 ± 3 |

*back-filled with PMP1$_{10}$

*E. coli* attachment to TiO$_2$ was reduced upon modification with PMP1$_{10}$, which is in general agreement with a previous study on attachment of *S. epidermidis* and *E. coli* to TiO$_2$ modified with a 20-mer Nme peptoid. The number of *E. coli* attached to PMP1-AMP was comparable to bare TiO$_2$ surfaces, whereas attachment to PMP1-C was much higher than PMP1-AMP and TiO$_2$ surfaces. Compared to PMP1$_{10}$, increased bacterial attachment to PMP1-AMP and PMP1-C surfaces could be explained either by direct interaction of the N-terminal peptoid sequences with the bacterial cell membrane, or through attachment of the bacteria to an adsorbed protein layer. In the case of PMP1-C the terminal peptoid is unlikely to be membrane active since this construct has no antibacterial properties in solution, suggesting a role for protein adsorption. With this in mind, protein adsorption to PMP1$_{10}$, and PMP1-AMP and PMP1-C back-filled with PMP1$_{10}$, was determined. The results shown in Table 4 indicate that while serum protein adsorption was increased on PMP1-AMP and PMP1-C substrates compared to PMP1$_{10}$ only substrates, the adsorbed masses are significantly lower than on unmodified TiO$_2$ sensors (p<0.05). That the peptoid side-chains of the N-terminal segments of PMP1-AMP and PMP1-C increase fouling by macromolecules is not surprising given the hydrophobic nature of the Nspe and Nssb residues in these sequences.

TABLE 4

Quantification of short-term (20 min) human serum protein adsorption on bare and modified $TiO_2$ sensors using OWLS. Standard deviations from the mean for 3 replicates are reported.

| Substrate | Adsorbed Serum Mass (ng/cm$^2$) |
| --- | --- |
| Bare $TiO_2$ | 342 ± 21 |
| PMP1$_{10}$ | 51 ± 7 |
| PMP1-AMP* | 119 ± 40 |
| PMP1-C* | 88 ± 30 |

*back-filled with PMP110

Staining of adhered *E. coli* with FITC revealed the highest percentage of bacterial cells with compromised membranes on the active PMP1-AMP polymer surface when compared to PMP1-C, PMP1$_{10}$ only and $TiO_2$ surfaces (Table 3). While the percent death on the PMP1$_{10}$ substrates was surprisingly high, overall cell adhesion is much lower than on the PMP1-AMP substrates; therefore the total number of FITC-stained bacteria on the active surface is more than ten times greater than on the PMP1$_{10}$ surfaces. Percent FITC-stained bacteria on the PMP1-C substrates was low and comparable to the control $TiO_2$ substrates, indicating no antimicrobial effects from this peptoid. While antibacterial activity was only demonstrated for *E. coli*, similar results are expected for *B. subtilis*, *S. epidermidis* and *P. aeruginosa* based on the MIC values determined for the ampetoids in solution (Table 1).

Figure 4:
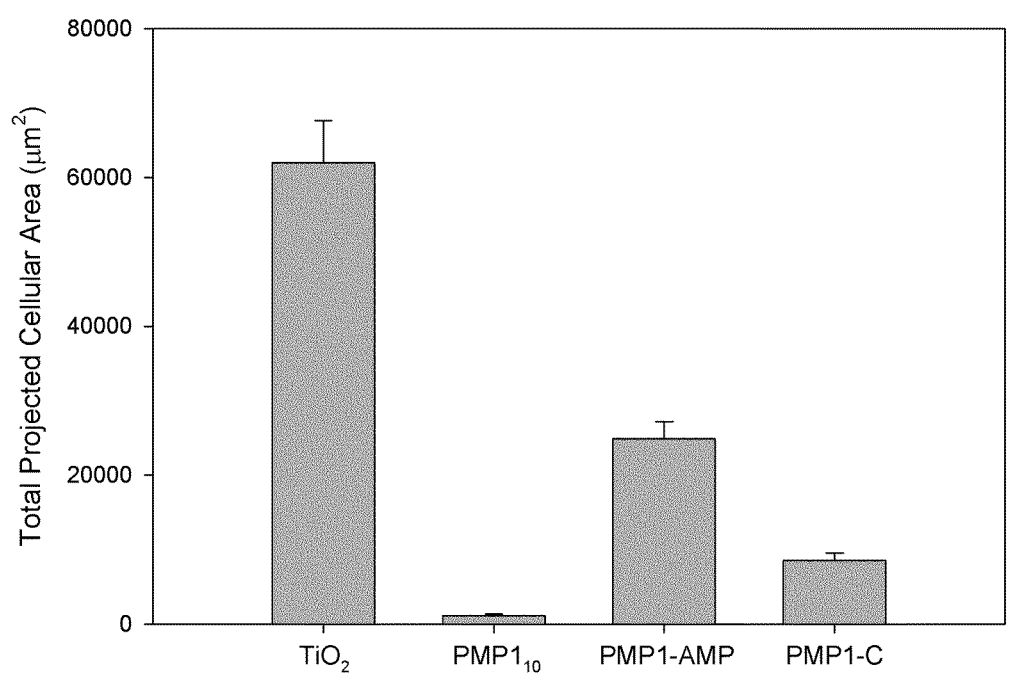
FIG. 4: Total projected cellular area for 4 h 3T3 fibroblast adhesion assay on bare TiO$_2$ and modified TiO$_2$ substrates.

To further assess the antifouling properties of these substrates a short-term fibroblast adhesion assay was conducted, the results of which are shown in FIG. 4. While the total projected area of adherent cells was greater on the polymer-modified surfaces containing the ampetoids than on the PMP1$_{10}$ substrates, all modified substrates had a significant reduction (p<0.05) in cell adhesion compared to bare $TiO_2$ substrates. The adherent cells appeared to be less spread on the ampetoid surfaces than the bare $TiO_2$ substrates, suggesting that while the fibroblasts may be able to weakly attach, they are not capable of spreading on the surface. These fibroblast adhesion results are consistent with the relative levels of serum protein adsorption (Table 4), suggesting that the modestly higher cell adhesion on the ampetoid-containing surfaces can be explained by the higher adsorbed protein on these surfaces.

The influence of polypeptoid chain length on antifouling component and corresponding properties was investigated, to further characterize the modified surfaces. The polymer thickness and surface density were compared to previous results on PEG-based systems in an attempt to better understand the packing of polypeptoid chains on surfaces. Although short-term protein fouling was found to be independent of the peptoid chain length, the shortest chain length peptoid became fouled with fibroblast cells within days, whereas the longer peptoid chains remained cell-free for several weeks. These findings show a relationship between adsorption reduction and the structure of the polypeptoid layer and suggests that in the case of very short chain length, the fouling by cells may be due to a kinetic effect on protein adsorption, while the surface coverage for longer peptoids may be sufficient for the full thermodynamic protection of the surface from protein adsorption.

Figure 5:
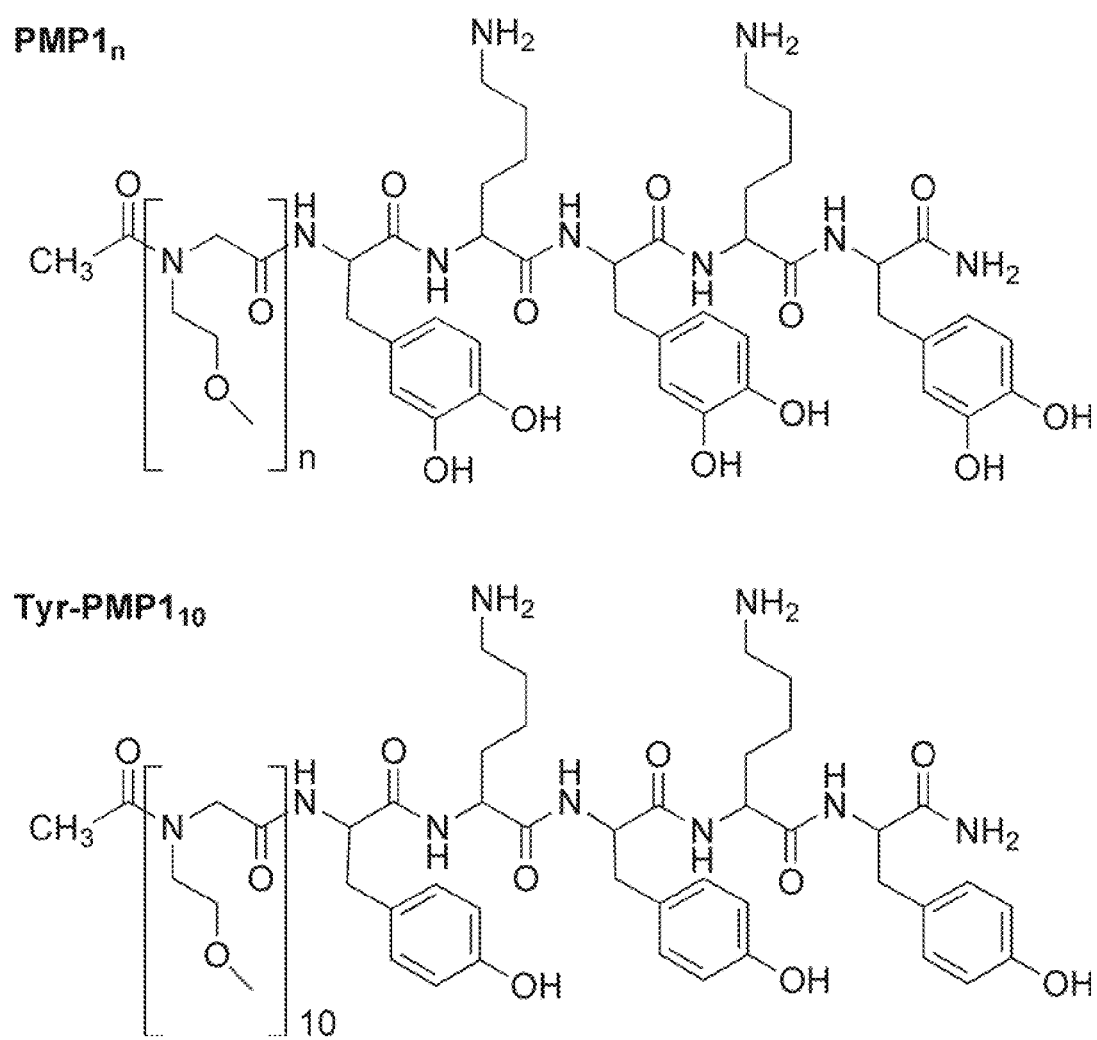
FIG. 5: Chemical structures of peptidomimetic polymers (PMP1$_n$), where n=10, 15, 20, 30, or 50 and Tyr-PMP1$_{10}$.

The particular polypeptoid polymers investigated were designed based on the superior performance of the aforementioned PMP1, a peptidomimetic polymer consisting of a DOPA, and lysine pentapeptide anchor coupled to 20 N-methoxyethyl glycine residues. The chemical structures of the polymers with varying chain lengths (PMP1$_n$) are shown in FIG. 5. The role of the DOPA residues in the pentapeptide was revealed through a polymer analog that contained tyrosine residues in place of the DOPA residues in the pentapeptide anchor coupled to 10 N-methoxyethyl glycine residues (Tyr-PMP1$_{10}$); the structure of this polymer is also shown in FIG. 5. Characterization data (RP-HPLC and MALDI-MS) for the purified polymers are available, but not shown.

The polymers were adsorbed onto $TiO_2$ substrates from buffer A at 50° C., corresponding to the previously reported marginal solvation conditions for PMP120, which should allow for greater grafted polymer density by reducing chain repulsion. While these adsorption conditions may not be optimal for all other chain lengths in the study, for experimental consistency, this modification condition was used for all experiments. The thicknesses of the polymer coatings adsorbed onto the $TiO_2$ surfaces as measured by spectroscopic ellipsometry are reported in Table 5. Average thickness values for the polymer-modified surfaces appear to increase with number of peptoid residues, but statistically significant differences (p<0.02) are detected only between PMP1$_{50}$ substrates and the shorter polymers, suggesting that small increases in chain length do not have a measurable effect on polymer thickness. The Tyr-PMP1$_{10}$ modified substrates had a significantly (p<0.02) thinner polymer coating compared to all DOPA-containing polymers, suggesting that either the polymer was not able to adsorb to the substrate or the adhesive strength was weak and the polymer was easily displaced by subsequent rinsing and drying steps. Reduction in the interaction strength is expected for the tyrosine-containing polymers compared to the DOPA-containing polymers based on AFM experiments, which demonstrated that the strong interactions between DOPA and $TiO_2$ surfaces were much higher than the interaction strength of tyrosine and $TiO_2$ surfaces.

TABLE 5

Polymer coating thickness measured by ellipsometry for polymer-modified $TiO_2$ substrates.

| Substrate | Coating thickness (Å) |
| --- | --- |
| PMP1$_{10}$ | 28.5 ± 3.5 |
| PMP1$_{15}$ | 32.5 ± 4.3 |
| PMP1$_{20}$ | 33.6 ± 4.6 |
| PMP1$_{30}$ | 34.1 ± 3.5 |
| PMP1$_{50}$ | 41.5 ± 5.1 |
| Tyr-PMP1$_{10}$ | 3.7 ± 0.6 |

Polymer adsorption was also characterized by in situ OWLS adsorption. This technique allows for highly sensitive (<0.5 ng/cm$^2$) measurement of mass adsorption per area in a flow-through cell device. Average mass results for three independent experiments for adsorption of each polymer on $TiO_2$-coated waveguides are shown in Table 6. As suggested by ellipsometry results, the mass of the polymer coating increases with increasing chain length and is significantly lower for Tyr-PMP1$_{10}$. These mass adsorption values were used to determine the surface density of polymer chains (σ) using the following equation:

$$\sigma = \frac{N_A m_A}{M_w},$$

where $N_A$ is Avogadro's number, mA is the measured mass of adsorbed polymer (in g/nm$^2$), and $M_w$ is the molecular weight of the polymer. While longer chain length polymers result in greater mass adsorption, this correlates to decreased surface density of polymer chains on the surface. A decrease in the polymer density does not appear to decrease fouling resistance, most likely because the longer chains allow more peptoid units to pack in each area. As the polymer surface coverage increases, a decrease in protein adsorption should be seen due to the steric barrier from the polymer layer that the adsorbing proteins encounter.

TABLE 6

Polymer mass adsorption measured by OWLS with corresponding molecular weights ($M_w$) and calculated density of polymer chains ($\sigma$).

| Polymer | Adsorbed mass (ng/cm$^2$) | $M_w$ | $\sigma$ (#/nm$^2$) |
| --- | --- | --- | --- |
| PMP1$_{10}$ | 359.7 ± 17.7 | 2003 | 1.08 |
| PMP1$_{15}$ | 412.0 ± 67.6 | 2578 | 0.96 |
| PMP1$_{20}$ | 456.0 ± 77.9 | 3156 | 0.87 |
| PMP1$_{30}$ | 510.0 ± 24.6 | 4304 | 0.71 |
| PMP1$_{50}$ | 552.3 ± 14.6 | 6610 | 0.50 |
| Tyr-PMP1$_{10}$ | 50.7 ± 8.3 | 1956 | 0.16 |

The polypeptoid backbone structure varies significantly from that of PEG; therefore, similar calculations for radius of gyration and molecular spacing cannot be made using the same parameters that are reported for PEG in literature. However, the polymer surface densities can be compared among different polymer systems in order to attempt to better understand fouling resistance of such coatings. PEG-containing surface coatings, investigated in the literature ranged, in layer thickness from 2 to 22 nm and chain density from 0.004 to 0.12 chains/nm$^2$ for either covalently grafted or strongly adsorbed polymers. (The PLL-g-PEG system used on Nb$_2$O$_5$ substrates achieved surface densities of 0.9, 0.5, and 0.3 chains/nm$^2$ for 1, 2, and 5 kDa PEGs.) Comparisons of PMP1 polymer densities to equivalent mass PEGs suggest that the PMP1 polymers are able to adsorb at nearly twice the density of the PLL-g-PEG system. The surface density of mPEG-DOPA$_3$ neared 50 EG/nm$^2$ (~0.44 chains/nm$^2$ for PEG-5000), with a threshold for protein adsorption demonstrated around 15-20 EG/nm$^2$ (~0.13-0.18 chains/nm$^2$). Thus, the poor fouling resistance of the Tyr-PMP1$_{10}$ substrates should be expected with a polymer density of 0.16 chains/nm$^2$. Molecular spacing calculations indicated that the surfacebound in PEG-DOPA$_3$ chains were in a brushlike structure at these high surface densities; the structural conformation of the polypeptoid polymers has not been determined, but a similar brushlike structure is expected, as it is shown by the predictions of the theory (see FIG. 9). The surface density results for the polypeptoid polymers are relatively high compared to PEG systems, suggesting that the MAP-inspired anchoring strategy allows for strong attachment to TiO$_2$ and formation of densely packed polymer layers.

Figure 6:
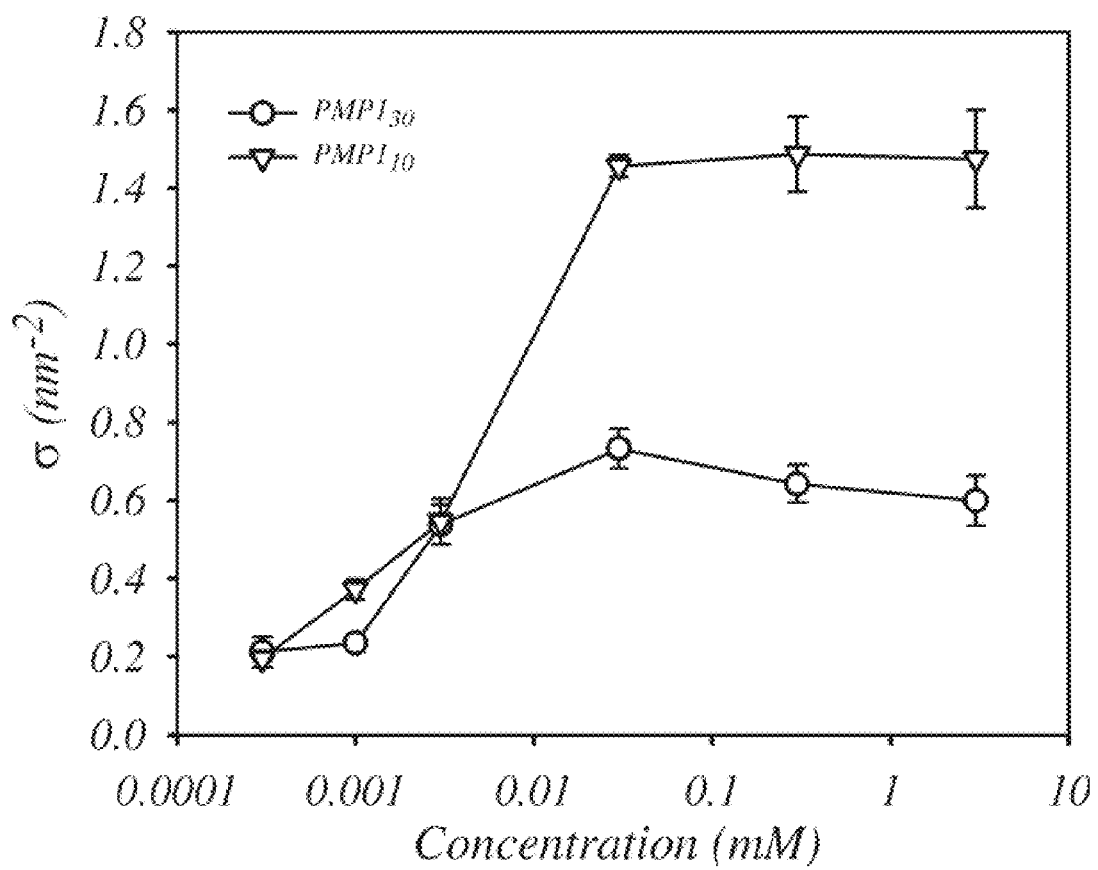
FIG. 6: Polymer chain density as a function of polymer solution concentration for PMP1$_{10}$ in UP H$_2$O.

To more closely study the adsorption of the polypeptoid polymers onto TiO$_2$ substrates, experiments were conducted using a range of polymer concentrations for PMP1$_{10}$ in H$_2$O. Surface density is plotted as a function of polymer concentration in FIG. 6. Results indicate that the density increases with concentration but appears to level off at higher concentrations.

Figure 7:
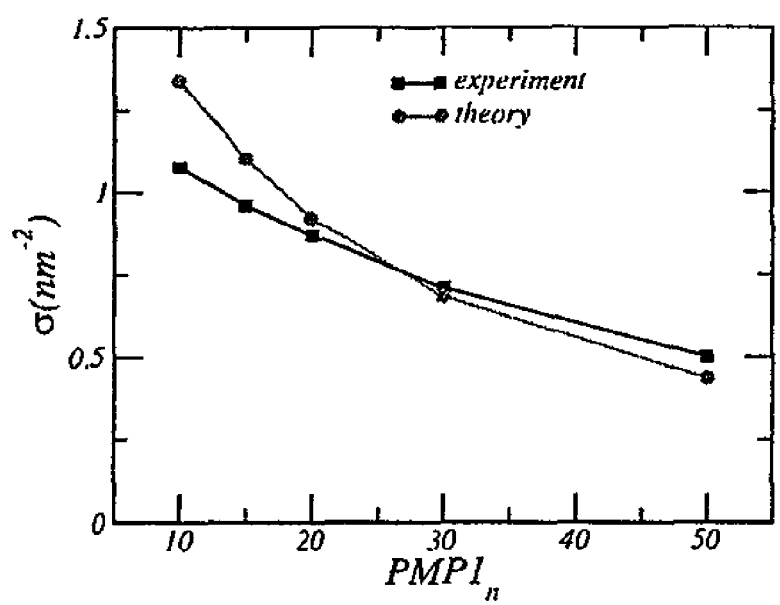
FIG. 7: Experimental and predicted polymer surface densities as a function of the chain length of the polypeptoid.

The next step is to compare the predictions from the molecular theory with the measured amount of polypeptoid on the surface (Table 6). To this end, FIG. 7 shows the amount of polymer adsorbed as a function of the length of the peptoid. The predictions of the theory are in good agreement with the experimental observations. The trends are identical in both cases, i.e., the amount of polypeptoid adsorbed decreases as the peptoid chain length increases. This result is not unexpected since the anchoring group, the DOPA-Lys pentapeptide, is identical in all cases and therefore the driving force for binding to the surface should be the same. However, as the chain length increases, the repulsions between the peptoids increases and thus less polymer can be attached with the same driving force.

Figure 8A:
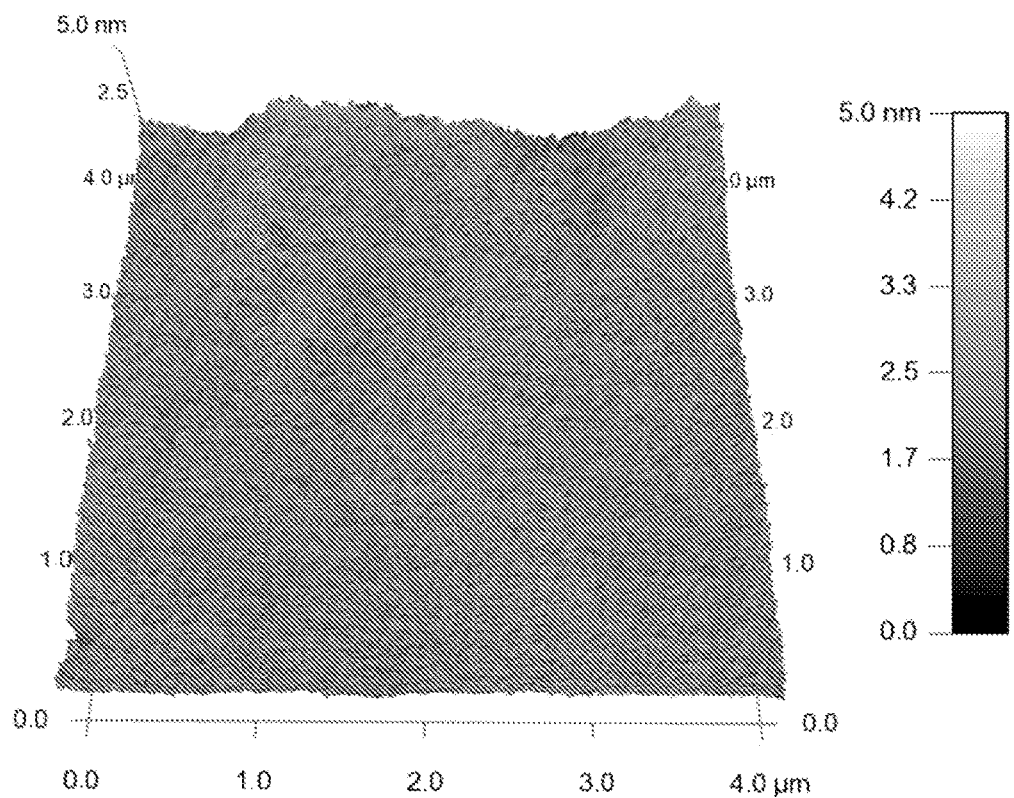
FIG. 8: AFM images of PMP1$_{50}$ modified substrates (pH 6) (A) and (B).
Figure 8B:
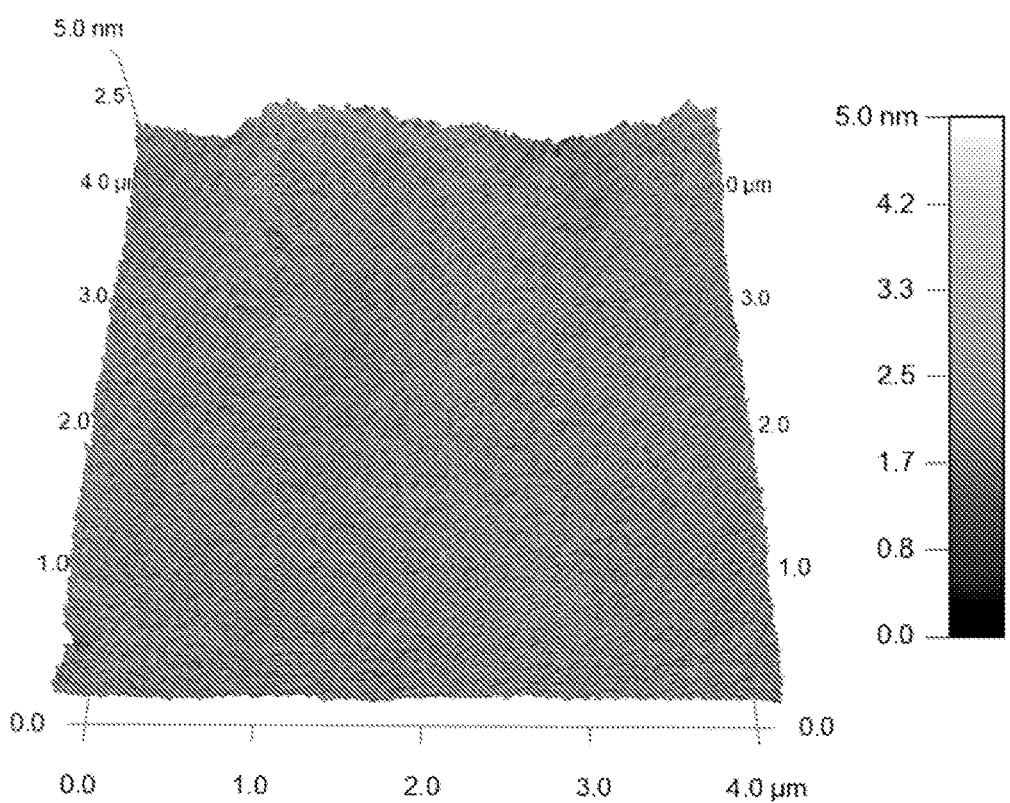

To better understand the surface architecture of polymer-modified surfaces, tapping-mode AFM was used to image PMP1$_{50}$ substrates under dry and aqueous conditions (FIG. 8). The dry substrate had an average rms roughness of 161±58 pm, and the roughness of the wet substrate was similar (rms roughness of 193±8 pm). These low roughness values and images demonstrate that homogeneous polymer layers can be created using these polypeptoid polymers. Similar roughness values were reported for PEG surfaces on glass. To determine the hydrated thickness of the polymer coatings, a scratch was made in the coating using a clean surgical blade, and then the area was imaged using tapping mode. The change in height between the scratched surface and the polymer coating was assumed to be the thickness of the polymer coating. The experiments were repeated for the same surfaces after drying with N$_2$. The average dry thickness for PMP1$_{50}$ is 5.2±0.3 nm, and the average thickness under aqueous conditions is 10.4±0.8 nm, suggesting a doubling of polymer thickness when hydrated. Using similar AFM imaging methods, the literature reported a dry film thickness of 10-20 nm and a hydrated film thickness of 50-100 nm for PEG coatings on glass. Using the contour length for amino acids (0.34 nm/residue), the calculated maximum thickness for PMP1$_{50}$ is 17 nm. Taking into account this calculated thickness, a hydrated surface thickness of 10 nm is quite plausible.

Figure 9:
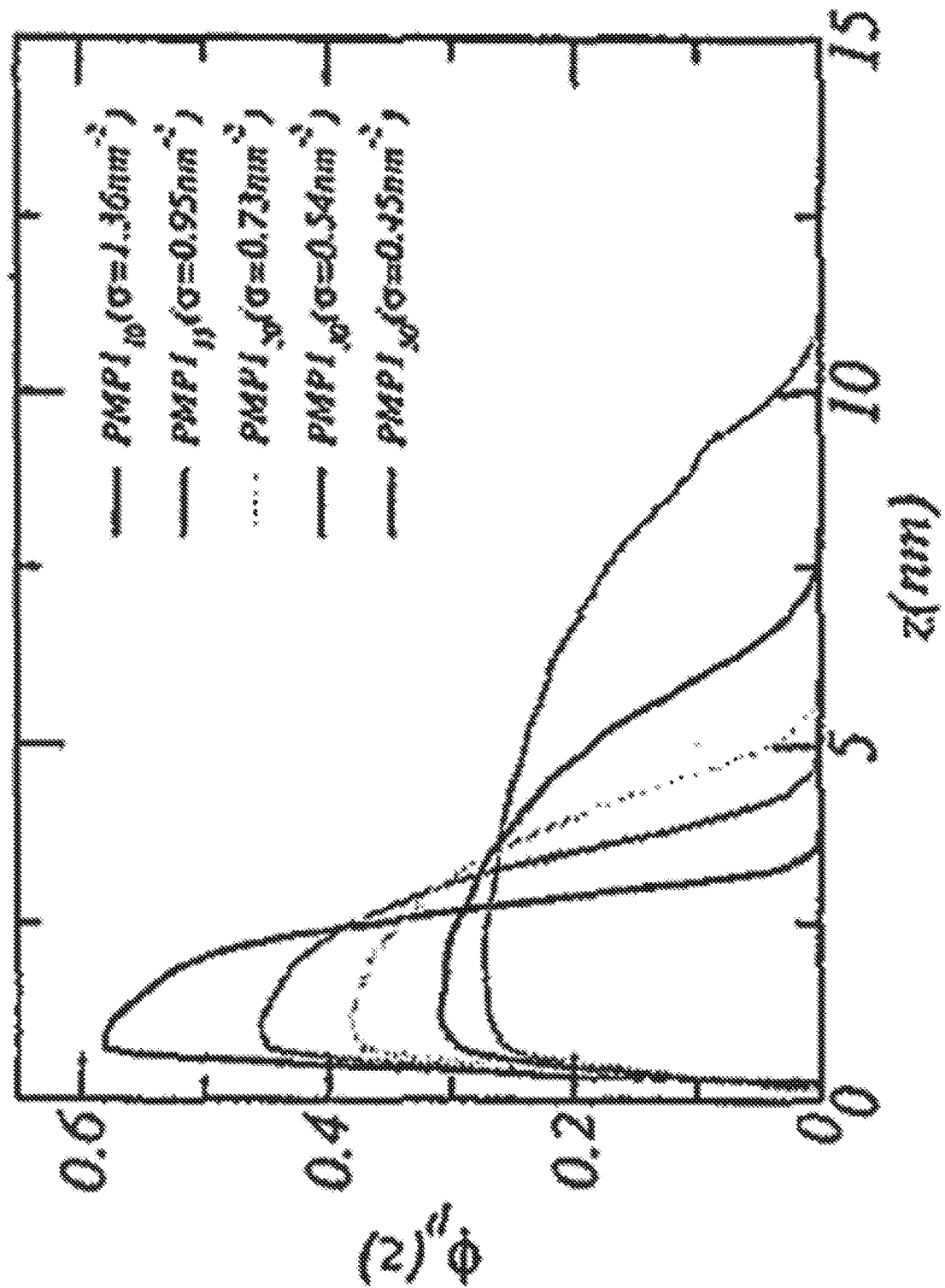
FIG. 9: Volume fraction profile (segmental density distribution) of the polypeptoids as a function of the distance from the surface. The different conditions correspond to the amount of polypeptoid adsorbed experimentally with the values as marked in the legend.

More detailed information on the structure of the grafted peptoids can be obtained by looking at the predictions of the molecular theory for the volume fraction profile of the peptoid for the measured surface coverage of polymers. This is shown in FIG. 9 for the five different polymers at the experimentally measured surface coverages. The peptoid segment profile shows a depletion region very close to the surface due to the presence of the adsorbed pentapeptide. The profiles show a stretched configuration with high local densities due to the bulky nature of the peptoid side groups. Interestingly, the local volume fraction in the region of maximal density is higher for the short polypeptoids. However, the films are thicker as the chain length increases. One can understand these two features by recalling that the strength of the binding to the surface is the same for all the different polymers. Therefore, the total repulsion between the peptoids at equilibrium needs to be the same. This is achieved by packing more polymers of short chain length with higher local segmental density. Note that this is a simple explanation since the full calculation also accounts for the loss of conformational entropy, which is a strong function of the chain length. Interestingly, the structure of the PMP1$_{50}$ predicted by the theory corresponds to a thickness slightly larger than 10 nm, in excellent agreement with the AFM observations. As we will discuss below, the structure of the different polymer layers is directly responsible for the nonfouling capabilities of the film.

TABLE 7

Average protein-adsorption values with standard deviations for serum and lysozyme adsorption measured by OWLS.

| Substrate | Adsorbed mass (ng/cm$^2$) | |
|---|---|---|
| | Serum | Fibrinogen |
| Bare TiO$_2$ | 342 ± 21 | 521 ± 61 |
| PMP1$_{10}$ | 51 ± 7 | 4 ± 2 |
| PMP1$_{15}$ | 53 ± 38 | 11 ± 2 |
| PMP1$_{20}$ | 15 ± 15 | 7 ± 3 |
| PMP1$_{30}$ | 28 ± 10 | 3 ± 3 |
| PMP1$_{50}$ | 34 ± 13 | 4 ± 3 |
| Tyr-PMP1$_{10}$ | 187 ± 77 | 319 ± 103 |

OWLS was also used for short-term protein-adsorption experiments with fibrinogen and human serum; the results are shown in Table 7. Protein adsorption values on unmodified TiO$_2$ sensors were comparable to published OWLS data for serum and fibrinogen; protein adsorption results on all PMP1-modified sensors were significantly lower (p<0.05) than unmodified TiO$_2$, but no statistically significant differences were observed between the PMP1-modified surfaces. The adsorbed serum masses for all PMP1-modified surfaces are similar to values for PEG coatings and other PMP coatings. Fibrinogen adsorption on the polymer-modified substrates is near to the ~5 ng/cm$^2$ threshold, below which activation of the pathways for blood coagulation does not occur, suggesting use of the coatings for blood contacting applications where prevention of thrombosis is desired. Serum and fibrinogen adsorption values on the Tyr-PMP1$_{10}$-modified sensors were significantly greater than the values for PMP1-modified sensors, as was expected based on the thinner polymer coating. PMP1 chain lengths of 10-50 repeat units are equally suited for short-term protein resistant surfaces, but further experiments are necessary to predict long-term resistance. According to literature reports, increasing the polymer chain length slows the adsorption kinetics for proteins; thus protein adsorption on the different polymers may not be seen until much longer time scales (months to years).

Figure 10:
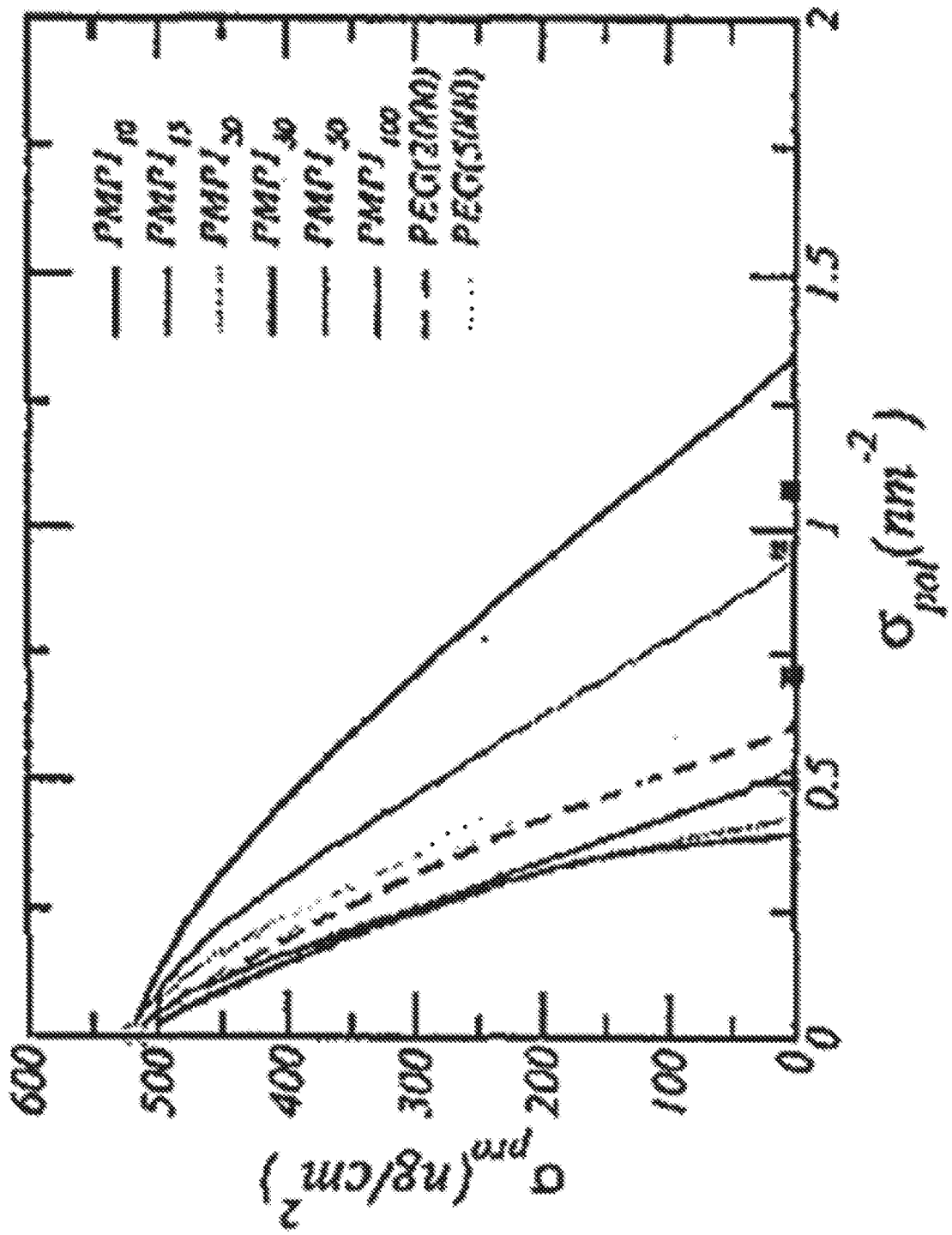
FIG. 10: Protein-adsorption isotherms. The amount of fibrinogen adsorbed as a function of the surface coverage of end-tethered polypeptide. The lines correspond to the theoretical predictions, while the symbols are the experimental observations. The point at $\sigma_{pol}=0$ corresponds to the bare TiO$_2$ surface.

The experimental observations for each polypeptoid length correspond to one value of the polymer surface coverage. To obtain a better understanding of how the polymers prevent protein adsorption, calculations are presented for the whole adsorption isotherms for each polypeptoid length. FIG. 10 displays the amount of fibrinogen adsorbed as a function of the amount of polypeptoid on the surface. For each chain length of polypeptoid, increasing the polymer surface coverage reduces the amount of protein adsorbed. Furthermore, for each polypeptoid length, there is an amount of grafted polymer, above which there is no more protein adsorption. The critical surface coverage for nonfouling decreases as the polymer chain length increases in the range of chain length used in the experimental observations, i.e., up to PMP1$_{50}$. Predictions for PMP1$_{100}$, which has not been studied experimentally, are also included. The ability of this long polymer to prevent protein adsorption is almost identical to that of PMP1$_{50}$. This is very much in line with previous predictions for model PEG that predict that once the polymer film thickness is larger than the size of the protein the polymer chain length has no effect on the equilibrium adsorption isotherm; however, it may have a very strong effect on the kinetics. As can be seen in FIG. 9, PMP1$_{30}$ forms a layer of thickness similar to the largest domain of fibrinogen, 6.5 nm. Thus, it can be expected that for polypeptoids with more than around 30-40 peptoids, the adsorption isotherm will be only weakly dependent on polymer size, as shown in FIG. 10.

In order to show the differences between polypeptoids and PEG, FIG. 10 shows the adsorption of fibrinogen as a function of surface coverage also for PEG-2000 and PEG-5000. In both cases, the ability of PEG to prevent protein adsorption at all surface coverages is less efficient than the polypeptoids with more than 20 units. Moreover, the predicted threshold for complete prevention of protein adsorption is above the surface coverage achieved with PLL-g-PEG of 0.5 and 0.3 chains/nm$^2$ for PEG-2000 and PEG-5000, respectively Thus, it would be expected that the nonfouling capabilities of these PEG layers to be time dependent.

All these results can be explained in terms of the ability of the flexible polypeptoid to reduce and reject protein adsorption due to the effective steric interactions that result from the excluded volume repulsions combined with the reduction in the available number of polymer conformations when proteins adsorb. This also explains the more effective capabilities of the polypeptoids as compared to PEG, for the same number of units, since the peptoids are bulkier than the ethylene oxide units, and therefore, offer more steric repulsion on a per unit basis.

It should be emphasized that the calculations represent equilibrium predictions. Namely, the theory assumes that the system has reached the thermodynamic preferred state of the system. However, it is not clear that the experimental observations, which are carried out over a relatively short time, reach the equilibrium state. Having this consideration, for all the experimental polypeptoids, except PMP1$_{10}$, the amount of polymer bound to the surface is larger than what is necessary for the complete thermodynamic prevention of protein adsorption, and indeed the measured amount of protein adsorption (shown as symbols in FIG. 10) is close to zero.

Figure 11:
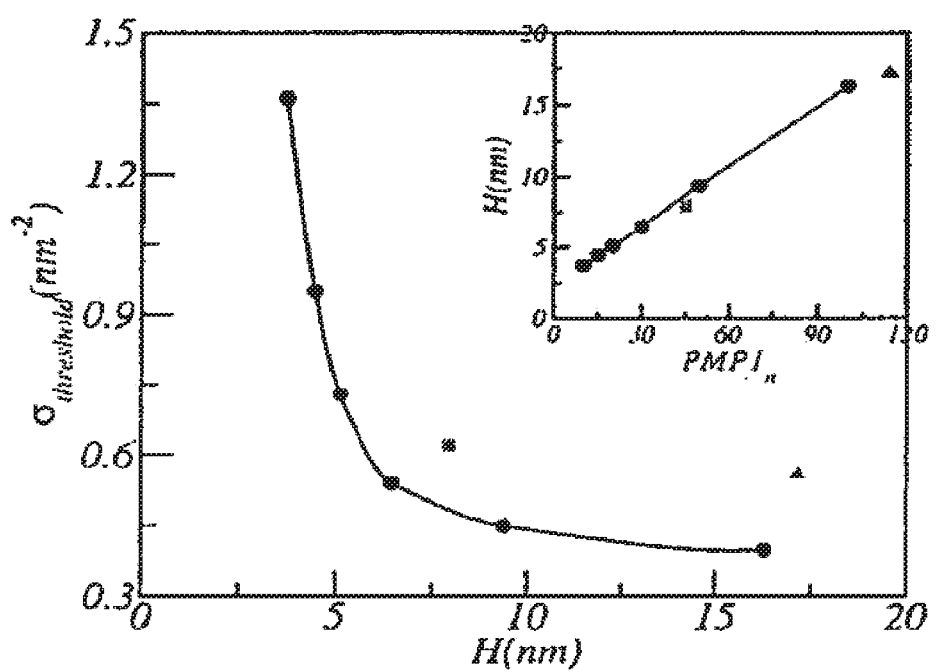
FIG. 11: Calculated threshold surface coverage for fibrinogen adsorption as a function of the polymer layer thickness for polypeptoids (circles), PEG-2000 (square), and PEG-5000 (triangle). The inset shows the calculated thickness as a function of the chain length for the same polymers, all at the threshold surface coverage.

The case of PMP1$_{10}$ is clearly different. The predicted isotherm shows that at the surface density of the experiment there will be a finite amount of adsorbed fibrinogen at equilibrium. However, the experimental observations show no adsorption. An important prediction from the theory is the chain length dependence of the threshold surface coverage to completely prevent protein adsorption. FIG. 11 shows the threshold surface coverage as a function of the film thickness, with the inset showing the film thickness as a function of polymer length. The thickness is calculated as $H=2\int\phi_{pol}(z)zdz/\int\phi_{pol}(z)dz$ which corresponds to the first moment of the polymer volume fraction profile. The thickness at the threshold surface coverage is linear with the polypeptoid chain length. Furthermore, the surface coverage threshold decreases very sharply for small thickness, but it levels off once the film thickness of the order of the protein size, in agreement with earlier predictions for PEG. These results show that molecular weight dependence for the equilibrium amount of protein adsorption is not very large once the polymer thickness is larger than the size of the protein; however, this weak dependence may not hold for the kinetics of protein adsorption, where both surface coverage and molecular weight play very important roles.

For cell adhesion studies, bare TiO$_2$ and polymer-modified TiO$_2$ substrates were seeded twice weekly with fresh 3T3 fibroblasts suspended in serum containing media. Cell attachment was quantified weekly for up to 7 weeks by live cell staining, fluorescence microscopy, and image analysis (FIG. 12). At the initial 4 h time point, fibroblasts attached readily to the unmodified TiO$_2$ substrates and the Tyr- PMP1$_{10}$-modified substrates, while all PMP1$_n$-modified substrates were highly resistant to adhesion. Fibroblasts formed confluent monolayers on the unmodified TiO$_2$ substrates and the Tyr-PMP1$_{10}$-modified substrates by day 14. The PMP1$_{10}$-modified substrates initially exhibited low levels of cell attachment but demonstrated a steady increase in adhesion, reaching confluent monolayers by week 7. All other PM1$_n$-modified substrates remained highly resistant to fibroblast adhesion throughout the experiment, which was expected for the 20-mer and longer chain lengths based on previously reported 5-month study.

The apparent threshold for long-term (7 weeks) fouling resistance is around 15 peptoid repeat units, which correlates to a dry polymer thickness of 32.5±4.3 Å from ellipsometry experiments and an adsorbed polymer mass of 412.0±67.6 ng/cm$^2$ from OWLS experiments. It can be inferred from these results that protein adsorption on polypeptoid polymers increases on time scales from months to years; therefore, if the 10-mer substrate was fouled by cells (and assumingly proteins) within 7 weeks in in vitro culture, we could predict that the 15-mer polymer would become fouled next, followed subsequently by the longer chain lengths. However, theoretical predictions show that for the experimental surface coverages the nonfouling capability of the surfaces with 15-mer polymer (and longer) are time independent, i.e., equilibrium. Importantly, cell adhesion results also support the previous claim that short-term (minutes to hours) protein-adsorption experiments may not always be the most reliable predictors of long-term (days, months, and years) biofouling events.

A more accurate prediction of protein (and cell) surface fouling can be made by using the theoretical results presented in FIG. 10. According to the predictions, only PMP1$_{10}$ is tethered at a surface coverage lower than the minimal needed for thermodynamic prevention of protein adsorption. Therefore, that surface should foul, as demonstrated in experiments. The time scale for fouling can be determined as shown in earlier work, and the time scale of days is not surprising. The predictions in FIG. 10 also show that none of the other surfaces should foul within the time frame of the current experiments since they are in the regime where thermodynamic control of protein adsorption is achieved. Thus, it can be expected that in those cases biofouling will not occur even in very long time scales.

EXAMPLES OF THE INVENTION

The following non-limiting examples and data illustrate various aspects and features relating to the compounds, articles and/or methods of the present invention, including the preparation of various antimicrobial compounds and their assembly on representative articles of manufacture, as are available through the synthetic methodologies described herein. In comparison with the prior art, the present compounds, articles and/or methods provide results and data which are surprising, unexpected and contrary thereto. While the utility of this invention is illustrated through the use of several antimicrobial compounds and ampetoid, antifouling and/or anchor components which can be used therewith, it would be understood by those skilled in the art that comparable results are obtainable with various other antimicrobial compounds and ampetoid/anti-fouling/anchor components, as are commensurate with the scope of this invention.

Materials for Examples 1-8

The primary amines for peptoid synthesis, 2,2,2-trifluoroethylamine, (S)-(−)-1-phenylethylamine, (S)-(+)-sec-butylamine, methoxyethylamine and 1,4-diaminobutane were purchased from Aldrich (Milwaukee, Wis.). Dimethylforinamide (DMF), diisopropylethylamine (DIPEA), acetonitrile, N-morpholinopropanesulfonic acid (MOPS) buffer salt, 4-(2-hydroxyethyl)piperazine-1-ethanesulfonic acid (HEPES) buffer salt, 2-propanol, 1,1'-dioctadecyl-3,3,3', 3'tetramethylindocarbocyanine perchlorate (DiI) and fluorescein 5(6)-isothiocyanate (FITC) were also purchased from Aldrich (Milwaukee, Wis.). Rink amide MBHA resin was purchased from AnaSpec (San Jose, Calif.). Fmoc-Lys (Boc)-OH, Fmoc-Dopa(acetonide)-OH, and Fmoc-Pro-OH were purchased from Novabiochem (San Diego, Calif.). A protected submonomer (N-tert-butoxycarbonyl-1,4-butanedi amine) was synthesized according to the published procedure (Krapcho & Kuell, 1990), while all other primary amines for peptoid synthesis were used as purchased. Acetic anhydride, 2-(1H-Benzotriazole-1-yl)-1,1,3,3-tetramethylaminium hexafluorophosphate (HBTU), and N-methylpyrrolidone (NMP) were purchased from Applied Biosystems (Foster City, Calif.). Trifluoroacetic acid (TFA) was obtained from Acros Organics (Belgium). Silicon wafers were purchased from University Wafer (South Boston, Mass.). Glass microscope slides and Lab-tek two-well slide chambers were purchased from Fisher Scientific (Pittsburgh, Pa.). 3T3-Swiss albino fibroblasts, Dulbecco's modified Eagle's medium, fetal bovine serum, penicillin/streptomycin, trypsin-EDTA, and *Escherichia coli* (ATCC 35218), *Bacillus subtilis* (ATCC 6633), *Staphylococcus epidermidis* RP62A (ATCC 12228) and *Pseudomonas aeruginosa* (ATCC 700829) were obtained from American Type Culture Collection (Manassas, Va.). Mueller-Hinton broth (MHB) and agar were purchased from Becton, Dickinson and Co. (Sparks, Md.). Lyophilized whole human serum (Control Serum N) was purchased from Roche Diagnostics (Indianapolis, Ind.). Ultrapure water (U.P. H$_2$O) used for all experiments was purified (resistivity≥18.2 MΩ-cm, total organic content ≤5 ppb) with a NANOpure Infinity System from Bamstead/Thermolyne Corp. (Dubuque, Iowa).

Example 1

Synthesis

Polymer sequences and peptoid monomer side chains and amino acids are shown in FIG. 1. Synthesis was performed on a C S Bio 036 (C S Bio Co., Menlo Park, Calif.) automated peptide synthesizer according to the previously described procedure (Statz et al, 2005). First, a C-terminal Dopa-Lys-Dopa-Lys-Dopa peptide was synthesized on rink amide MBHA resin using conventional Fmoc strategy of solid-phase peptide synthesis; this pentapeptide functions as an adhesive anchor for immobilization of the peptoid onto surfaces (See, the incorporated co-pending '107 application). A 20-mer N-methoxyethyl glycine (Nme) polypeptoid portion was then synthesized using a submonomer protocol (Zuckermann et al., 1992) and the resin was split. For PMP1-AMP and PMP1-C, submonomer synthesis was continued to add peptoid AMP(H-NLys-Nspe-Nspe-NLys-Nspe-Pro-[NLys-Nspe-Nspe]$_2$—NH$_2$) or peptoid C(H-[NLys-Nssb-Nssb]$_4$-NH$_2$) (See, Chongsiriwatana et al., supra, and the incorporated co-pending '034 application), respectively, onto the N-terminus of the Nme polypeptoid. During synthesis of PMP1-AMP and PMP1-C, a single residue of N-(2,2,2-trifluoroethyl)glycine (Ntfe) was added between the peptide and peptoid fragments, as a label for XPS compositional analysis. PMP1$_{10}$ consisted of a 10-mer sequence of Nme conjugated to the adhesive pentapeptide anchor, and was used as a passive 'backfilling' component in surfaces pre-adsorbed with PMP1-AMP.

Polymers were cleaved from the resin and the amino acid side-chains were deprotected by treating the resin with 95% (v/v) TFA, 2.5% $H_2O$ and 2.5% TIS for 10 minutes, after which the cleaved polymer was removed by filtering and rinsing several times with TFA. Solvent was removed using a rotary evaporator; the product was dissolved in 50/50% water/acetonitrile, frozen and lyophilized. The crude products were purified by preparative reversed-phase high performance liquid chromatography (RP-HPLC) (Waters, Milford, Mass.) using a Vydac C18 column. The purity of each final product was confirmed by RP-HPLC and matrix-assisted laser desorption/ionization mass spectrometry (MALDI-MS) (Voyager DE-Pro, Perspective Biosystem, MA).

Example 2

Antibacterial Activity in Solution

The minimum inhibitory concentration (MIC) for each polymer was determined according to Clinical Laboratory Standards Institute (CLSI) broth microdilution protocols (M7-A6). The procedure explained previously was followed (Chongsiriwatana et al., supra); briefly, serial dilutions of the polymers were prepared in Mueller-Hinton broth (MHB) in 96-well microtiter plates and bacterial inoculum in MHB was added to each well (~5.0×10$^4$ CFU/well). Optical density was monitored at 590 nm for 16 h at 35° C. The MIC was defined as the lowest concentration of peptoid/polymer necessary to completely inhibit bacterial growth for 16 h; experiments were repeated three times in duplicate for each bacterial strain including *E. coli, B. subtilis, S. epidermidis* and *P. aeruginosa*.

Example 3

CD Spectroscopy

CD measurements were conducted on a Jasco model 715 spectropolarimeter, using a quartz cylindrical cell (path length=0.02 cm). Samples were dissolved at a concentration of 50 µM in 10 mM Tris-HCl (pH=7.4). Scans were measured at 100 mm/min between 185 and 280 nm at 0.2 nm data pitch, 1 nm bandwidth, 2 s response, and 100 mdeg sensitivity. The plots contain the average data from 40 spectral accumulations.

Example 4

Surface Modification

Silicon wafers and glass slides were coated with a 20 nm-thick layer of $TiO_2$ by electron beam evaporation (Edwards Auto306; <10$^{-5}$ Torr); the coated wafers were cut into 1-cm$^2$ pieces. The substrates were cleaned ultrasonically for ten minutes in 2-propanol, dried under $N_2$, and then exposed to $O_2$ plasma (Harrick Scientific, Ossinging, USA) at ≤150 Torr and 100 W for three minutes. Optical waveguide lightmode spectroscopy (OWLS) waveguides were purchased from MicroVacuum Ltd. (Budapest, Hungary) and coated with a 10 nm-thick layer of $TiO_2$ by electron beam evaporation as described above. Sensors were cleaned following the same procedure as $TiO_2$ substrates. After use, OWLS waveguides were regenerated for subsequent use by 10-minute sonication cycles in 0.1 M HCl, U.P. $H_2O$ and 2-propanol followed by exposure to $O_2$ plasma to remove adsorbates.

Clean substrates and sensors were immersed in a 0.5 mg/ml solution of the appropriate ampetoid in U.P. $H_2O$ at 25° C. After 2 hours, substrates were removed and rinsed with U.P. $H_2O$ to remove any unbound polymer, and then dried in a stream of filtered $N_2$. Next the substrates were immersed in a 1.0 mg/ml solution of $PMP1_{10}$ in 3 M NaCl buffered with 0.1M MOPS, pH=6 (C.P. buffer) at 50° C. for 6 hours. After modification, substrates were extensively rinsed with U.P. $H_2O$ to remove any unbound polymer, and then dried in a stream of filtered $N_2$.

Example 5

X-ray Photoelectron Spectroscopy (XPS)

Survey and high resolution XPS spectra were collected on an Omicron ESCALAB (Omicron, Taunusstein, Germany) configured with a monochromated Al Kα (1486.8 eV) 300-W X-ray source, 1.5 mm circular spot size, a flood gun to counter charging effects, and an ultrahigh vacuum (<10$^{-8}$ Torr). Substrates were prepared and analyzed as previously described in the literature.

Example 6

Optical Waveguide Lightmode Spectroscopy (OWLS)

OWLS was used to determine the optimum adsorption conditions for the polymers on $TiO_2$ surfaces. Clean $TiO_2$ sensors were inserted into the measurement head of an OWLS110 (MicroVacuum Ltd.) and exposed to the appropriate buffer solution through the flow-through cell (16 µl volume) for several hours to allow for equilibration. Ampetoid solutions were injected into the flow-through cell in stop-flow mode and allowed to adsorb for various times. The waveguide sensors were subsequently rinsed with buffer, and allowed to equilibrate for another 30 minutes. Between polymer adsorption steps, buffers were exchanged and the system was allowed to equilibrate for at least 10 hours. The measured incoupling angles, $\alpha_{TM}$ and $\alpha_{TE}$ were converted to refractive indices $N_{TM}$ and $N_{TE}$ by the MicroVacuum software, and changes in refractive index at the sensor surface were converted to adsorbed mass using de Feijter's formula (de Feijter et al., 1978). The refractive indices of solutions were measured using a refractometer (J157 Automatic Refractometer, Rudolph Research) under identical experimental conditions. A refractive index value of 1.35616 was used for the C.P. buffer, and 0.159 cm$^3$/g and 0.129 cm$^3$/g were used for dn/dc values for the ampetoids and $PMP1_{10}$, respectively.

OWLS was also used for in situ protein adsorption experiments; $TiO_2$ coated waveguide sensors were modified with the polymers as explained previously. After adequate equilibration of the sensors in HEPES buffer, human serum solution was injected and allowed to adsorb for 20 minutes at 37° C. before rinsing with HEPES buffer. A refractive index value of 1.33127 was used for the HEPES buffer, and a standard value of 0.182 cm$^3$/g was used for dn/dc in the protein-adsorption calculations (Pasche et al., 2003). Averages and standard deviations from 3 replicates are reported. Statistical significance was assessed using a one-way ANOVA and Tukey's post-hoc test with 95% confidence intervals (SPSS, Chicago, Ill.).

Example 7

Antibacterial Activity on Surfaces

*E. coli* were streaked from frozen stocks onto Mueller-Hinton agar and incubated overnight at 37° C. A few colonies were then used to inoculate 25 ml of sterile Mueller-Hinton broth (MHB) and grown overnight at 37° C. $TiO_2$-coated glass slides were modified with the polymers using the previously described procedure. Two-well chambers were clamped to the slides and sealed by injecting silastic resin, which was allowed to cure overnight. Slides were sterilized by exposure to UV light for 10 minutes. The bacterial suspension was concentrated by centrifugation and resuspended in PBS at a concentration of $5 \times 10^7$ CFU/ml; 2 ml of the *E. coli* suspension was added to each slide chamber. Slide chambers were covered and placed in a humidified incubator at 37° C.; after 2 h, nonadherent bacteria were removed by inverted centrifugation for 2 min at 30 rcf in sealed bags filled with PBS (Jensen et al., 2004). Adherent bacteria were stained with FITC (6 µg/ml) in PBS for 15 min at 37° C.; FITC has been observed to only penetrate into cells with compromised membranes. Slides were rinsed with PBS and imaged by confocal microscopy equipped with an inverted microscope (Leica TCS SP2). Phase contrast and fluorescent (488-nm band-pass filter for excitation of FITC) images were taken at identical locations to determine bacterial cell count and percent stained with FITC. The microscopy images were quantified using thresholding in ImageJ, and averages with standard deviations for at least nine images from one slide are reported. While slides were prepared in duplicate or triplicate and consistency was qualitatively confirmed between experimental samples, the reported counts and images were obtained from a single slide for each condition.

Example 8

Fibroblast Adhesion Assay

3T3-Swiss albino fibroblasts were maintained at 37° C. and 5% $CO_2$ in Dulbecco's modified Eagle's medium (DMEM) containing 10% fetal bovine serum (FBS) and 100 U/ml of penicillin/streptomycin. Immediately before use, fibroblasts of passage 12-16 were harvested using 0.25% trypsin-EDTA, resuspended in DMEM with 10% FBS and counted using a hemacytometer. Modified and unmodified $TiO_2$ substrates were sterilized by exposure to UV light for 10 minutes; cells were seeded on each substrate at a density of $2.9 \times 10^3$ cells/cm$^2$ and maintained in DMEM with FBS at 37° C. and 5% $CO_2$ for 4 hours, after which adherent cells were fixed in 3.7% paraformaldehyde for 5 minutes and stained with 5 µM 1,1'-dioctadecyl-3,3,3',3'tetramethylindocarbocyanine perchlorate (DiI) for epifluorescent microscope counting.

Quantitative cell attachment data were obtained by acquiring nine images (10× magnification) from random locations on each substrate using a Leica epifluorescent microscope (W. Nuhsbaum Inc., McHenry, Ill.) equipped with a SPOT RT digital camera (Diagnostics Instruments, Sterling Heights, Mich.). Three identical substrates for each experiment were analyzed, and total projected cellular area was quantified using thresholding in Metamorph (Molecular Devices, Downingtown, Pa.); the mean and standard deviation are reported. Statistical significance was assessed using a one-way ANOVA and Tukey's post-hoc test with 95% confidence intervals (SPSS, Chicago, Ill.).

Materials for Examples 9-17

Methoxyethylamine, tri-isopropylsilane (TIS), dimethylformamide, acetonitrile, N-morpholinopropanesulfonic acid (MOPS) buffer salt, fibrinogen, 4-(2-hydroxyethyl)piperazine-1-ethanesulfonic acid (HEPES) buffer salt, tris buffer salt, sodium tetraborate, 2-propanol, 1,1'-dioctadecyl-3,3,3', 3'-tetramethylindocarbocyanine perchlorate (DiI), and alpha-cyano-4-hydroxycinnamic acid matrix were purchased from Aldrich (Milwaukee, Wis.). Rink amide-MBHA resin LL, Fmoc-Lys(Boc)-OH, Fmoc-Tyr(tBu)-OH, and Fmoc-DOPA(acetonide)-OH were purchased from Novabiochem (San Diego, Calif.). Acetic anhydride and N-methylpyrrolidone were purchased from Applied Biosystems (Foster City, Calif.). Trifluoroacetic acid (TFA) was obtained from Fisher Scientific (Pittsburgh, Pa.). Silicon wafers were purchased from University Wafer (South Boston, Mass.). Lyophilized whole human serum (Control Serum N) was purchased from Roche Diagnostics (Indianapolis, Ind.). Calcein-AM was purchased from Molecular Probes (Eugene, Oreg.). 3T3-Swiss albino fibroblasts, Dulbecco's modified Eagle's medium (DMEM), fetal bovine serum (FBS), and penicillin/streptomycin were obtained from American Type Culture Collection (Manassas, Va.). Ultrapure water (UP $H_2O$) used for all experiments was purified (resistivity of $\geq 18.2$ MΩ·cm; total organic content of $\leq 5$ ppb) with a NANOpure Infinity System from Barnstead/Thermolyne Corp. (Dubuque, Iowa).

Example 9

Synthesis of Peptidomimetic Polymers

The peptidomimetic polymers were synthesized, as described previously, in the co-pending '107 application using a C S Bio 036 (C S Bio Co., Menlo Park, Calif.) automated peptide synthesizer. The five polymers of varying chain lengths were synthesized in one batch by removing portions of the resin from the reaction vessel at the appropriate coupling step. The C-terminal DOPA-Lys-DOPA-Lys-DOPA peptide anchor was first synthesized on a low loading rink amide resin using conventional Fmoc strategy of solid-phase peptide synthesis; the polypeptoid portion was then synthesized using a submonomer protocol. The Tyr polymer analog was synthesized according to the same procedure but using Fmoc-Tyr(tBu)-OH instead of Fmoc-DOPA(acetonide)-OH. Acetic anhydride was used to acetylate the N-terminus of the polypeptoid chain upon removal from the vessel; cleavage of the polymers from the resin and deprotection of the amino acid side chains was accomplished by treating the resin with 95% (v/v) TFA, 2.5% $H_2O$, and 2.5% TIS for 20 min. The cleaved polymer was then removed by filtering and rinsing several times with TFA, and the solvent was removed using a rotary evaporator; the oily product was dissolved in 50/50% water/acetonitrile, frozen, and lyophilized. The crude products were purified by preparative reversed-phase high performance liquid chromatography (RP-HPLC) (Waters, Milford, Mass.) using a Vydac C18 column, and purified fractions were frozen and lyophilized. The purity of each final product was confirmed by RP-HPLC and matrix-assisted laser desorption/ionization mass spectrometry (MALDI-MS) (Voyager DE-Pro, Perspective Biosystem, MA).

Example 10

Surface Modification

Silicon wafers were coated with a 20-nm-thick layer of $TiO_2$ by electron beam evaporation (Edwards Auto306; $<10^{-5}$ Torr), and the coated wafers were cut into 8×8 mm$^2$ pieces. The substrates were cleaned ultrasonically for 10 min in 2-propanol and dried under $N_2$. Surfaces were then exposed to $O_2$ plasma (Harrick Scientific, Ossining, N.Y.) at $\leq 150$ Torr and 100 W for 3 min. Optical waveguide light mode spectroscopy (OWLS) waveguides were purchased from MicroVacuum Ltd. (Budapest, Hungary) and coated with a 10-nm-thick layer of $TiO_2$ by electron beam evaporation as described above. Sensors were cleaned following the same procedure as $TiO_2$ substrates. After use, OWLS waveguides were regenerated for subsequent use by 10 min sonication cycles in 0.1M HCl, UP $H_2O$, and 2-propanol, followed by exposure to $O_2$ plasma to remove adsorbates.

Unless otherwise noted, the general approach used for surface modification involved immersion of clean substrates and sensors in a 0.3 mM solution of peptidomimetic polymer in buffer A (3M NaCl buffered with 0.1M MOPS, pH=6) at 50° C. for 24 h. After modification, substrates were extensively rinsed with UP $H_2O$ to remove any unbound polymer and then dried in a stream of filtered $N_2$.

Surface Characterization

Example 11

Spectroscopic Ellipsometry Measurements

Prior to modification, substrates were cleaned as described above and measured using an M-2000 spectroscopic ellipsometer (J. A. Woollam, Lincoln, Nebr.). Measurements were made at 65°, 70°, and 75° using wavelengths from 193 to 1000 nm. After modification, substrates were rinsed and dried as described above and measured again. The spectra were fit with multilayer models in the WVASE32 software (J. A. Woollam). Optical properties of the substrate were fit using a standard $TiO_2$ model, while properties of the polymer layer were fit using a Cauchy model ($A_n$=1.45, $B_n$=0.01, $C_n$=0). The obtained ellipsometric thicknesses represent the "dry" thickness of the polymer under ambient conditions. The average thickness and standard deviation of three or more substrates are reported for each polymer.

Example 12

OWLS

For in situ polymer-adsorption experiments, $TiO_2$ coated waveguide sensors were cleaned and inserted into the measurement head of an OWLS110 (MicroVacuum Ltd.) and exposed under static conditions to buffer A through the flow-through cell (16 µl volume) for at least 24 h to allow for equilibration. The measurement head was mounted on the sample chamber and heated to 50° C.; the signal was recorded to ensure a stable baseline. Polymer solution (1 ml total volume) was injected into the flow-through cell in stopflow mode. The waveguide sensor was exposed to the polymer solution for 4 h, subsequently rinsed with buffer A (2 ml), and allowed to equilibrate for another 30 min. Adsorption experiments with varying polymer concentrations were conducted in UP $H_2O$ at 25° C. using the same procedure.

The measured incoupling angles, $\alpha_{TM}$ and $\alpha_{TE}$ were converted to refractive indices $N_{TM}$ and $N_{TE}$ by the MICRO-VACUUM software, and changes in the refractive index at the sensor surface were converted to adsorbed mass using de Feijter's formula. The refractive indices of solutions were measured using a refractometer (J157 Automatic Refractometer, Rudolph Research) under identical experimental conditions. A refractive index value of 1.356 16 was used for Buffer A, and a value of 0.129 $cm^3/g$ was used for dn/dc in the polymer-adsorption calculations.

Example 13

Atomic Force Microscopy

Atomic force microscopy (AFM) measurements were performed on an Asylum MFP-3D instrument (Asylum Research, Santa Barbara, Calif.) installed on a Nikon TE2000 microscope. Silicon cantilevers (VISTAprobes, T300) were used for tapping-mode measurements in air and silicon nitride cantilevers (Veecoprobes, DNP-S20) were used for tapping-mode measurements in UP $H_2O$.

Example 14

X-Ray Photoelectron Spectroscopy

Survey and high-resolution x-ray photoelectron spectroscopy (XPS) spectra were collected on an Omicron ESCALAB (Omicron, Taunusstein, Germany) configured with a monochromated Al K$\alpha$ (1486.8 eV) 300 W x-ray source, 1.5 min circular spot size, a flood gun to counter charging effects, and an ultrahigh vacuum (<$10^{-8}$ Torr). The takeoff angle was fixed at 45°. Substrates were mounted on standard sample studs using double-sided Cu adhesive tape. Spectra were filled using CASAXPS software; specifically a Shirley background subtraction and the sum of 90% Gaussian and 10% Lorentzian function were used. Atomic sensitivity factors were used to normalize peak areas from high-resolution spectra to intensity values, which were then used to calculate atomic compositions.

Example 15

Protein Adsorption Experiments

Lyophilized human serum was reconstituted in water to reach the typical concentration in blood; fibrinogen from human plasma was dissolved at 3 mg/ml concentrations in buffer B (10 mM HEPES, 150 mM NaCl, pH=7.4). For in situ protein-adsorption experiments, $TiO_2$ coated waveguide sensors were modified with peptidomimetic polymers as explained previously. After equilibration of the OWLS baseline in buffer B, protein solution was injected and allowed to adsorb for 20 min at 37° C. before rinsing with buffer B. A refractive index value of 1.331 27 was used for buffer B, and a standard value of 0.182 $cm^3/g$ was used for dn/dc in the protein-adsorption calculations.

Example 16

Mammalian Cell Adhesion Experiments

3T3-Swiss albino fibroblasts were maintained at 37° C. and 5% $CO_2$ in DMEM containing 10% FBS and 100 U/ml of penicillin/streptomycin. Immediately before use, fibroblasts of passage 12-16 were harvested using 0.25% trypsin-EDTA, resuspended in DMEM with 10% FBS, and counted using a hemacytometer. Modified and unmodified substrates were placed in a 12-well tissue culture polystyrene plate and sterilized by exposure to UV light for 10 min, after which 1 ml of DMEM containing FBS was added to each well and incubated for 30 min at 37° C. and 5% $CO_2$. For the long-term experiment, the fibroblast cell suspension was diluted, and the cells were seeded on each substrate at a density of 2.9×$10^3$ cells/$cm^2$ and substrates were reseeded twice per week. For live cell staining, the medium was aspirated from each well to remove any nonadherent cells and phosphate buffered saline (PBS) was used to rinse the substrates and wells. Fibroblasts were stained with 2.5 µM calcein-AM in complete PBS for 1 h at 37° C.; substrates were transferred to new culture plates with fresh media and imaged weekly. After imaging, substrates were reseeded and placed back into the incubator; media were changed every 3 days. For short-term 4 h assays on varying surface chemistries, cells were plated at a density of $29 \times 10^3$ cells/cm$^2$; adherent cells were fixed in 3.7% para-formaldehyde for 5 min and stained with 5 µM DiI for epifluorescent microscope counting.

Quantitative cell attachment data were obtained by acquiring nine images (10× magnification) from random locations on each substrate using a Leica epifluorescent microscope (W. Nuhsbaum Inc., McHenry, Ill.) equipped with a SPOT RT digital camera (Diagnostics Instruments, Sterling Heights, Mich.). Three identical substrates for each experiment were analyzed for statistical purposes, resulting in a total of 27 images per time point for each modification. The microscopy images were quantified using thresholding in Metamorph (Molecular Devices, Downingtown, Pa.).

Example 17

Theoretical Approach

The theoretical approach applied is a molecular theory that has been shown to provide accurate information as compared to experimental observations for the structure and thermodynamics of tethered polymer layers (I. Szleifer, Curr. Opin. Colloid Interface Sci. 1, 416 (1996)) as well as in the determination of the amount of protein adsorption on surfaces with grafted PEG. The agreement with experimental observations is for oligomeric chains (J. Satulovslcy, M. A. Carignano, and I. Szleifer, Proc. Natl. Acad. Sci. U.S.A. 97, 9037 (2000)) as well as long polymers (49T. McPherson, A. Kidane, I. Szleifer, and K. Park, Langmuir 14, 176 (1998)) and at all polymer-grafting densities. It is believed that the approach is very appropriate to predict the amount of grafted polypeptoid end-adsorbed as well as the ability of the peptoid to prevent protein adsorption. For a complete discussion of the theoretical considerations leading to the results and conclusions discussed herein, see Statz, et al. Biointerphases, 4(2), June 2009, the entirety of which is incorporated by reference.

As demonstrated above, peptoids are promising alternatives to conventional antimicrobials because of their stability, ease of synthesis and low cytotoxicity. Results show that peptoid mimics of antimicrobial peptides can be immobilized onto surfaces, rendering these surfaces capable of compromising the membranes of attached bacteria. The antibacterial activity of the ampetoids was initially demonstrated in solution-based assays, and subsequently shown for E. coli when immobilized onto surfaces. Substrates modified with PMP1-AMP exhibited increased bacterial adhesion, and a significant percentage of the adherent bacteria had compromised membranes, indicating that the surface-immobilized ampetoids were capable of interacting with the bacteria. By modifying the surfaces with both the ampetoids and PMP1$_{10}$, the passive resistance to protein and mammalian cell fouling was improved compared to bare TiO$_2$, while maintaining sufficient ampetoid concentration for antibacterial activity. In certain embodiments, the benefits of having an active antibacterial component on the surface may outweigh the disadvantages of slightly increased bacterial adhesion. Fine-tuning the ratio of adsorbed passive and active components, or the composition of the active component, may provide a surface composition that combines even greater resistance to protein and bacterial adhesion with an antibacterial effect.

In particular, passive anti-fouling and anchor components, composed of a peptide anchor coupled to anti-fouling N-methoxyethyl glycines of varying repeat lengths, were determined to have significant antifouling properties when immobilized onto TiO$_2$ substrates. With respect to an antifouling component, minimum chain length of 15 peptoids was demonstrated for long-term (7 weeks) cell fouling resistance, suggesting that shorter polymer chain lengths provide less sufficient coatings to prevent adsorption of proteins to the underlying substrates for longer time scales.

As demonstrated, the use of a predictive molecular theory can be a very important component in the design of surface modifiers for nonfouling applications. Theory enables the prediction of the amount of polypeptoid bound to the surface and the ability of that surface to prevent protein adsorption. The optimal conditions for modification are such that the bound surface coverage is larger than the minimal coverage needed for thermodynamic prevention of protein adsorption. If the tethered polymers are at lower surface densities, long-term fouling will occur. The compromise between surface coverage and molecular weight in determining fouling capabilities depends on the chemical nature of the polymers and can be determined a priori with appropriate theoretical tools.

For some medical device applications, more sophisticated designs incorporating hydrolytic or enzymatic cleavage sites within the PMP1-AMP backbone can allow for cleavage of the antibacterial domain from the coating once the risk of post-operative infection had passed, leaving behind a protein and cell resistant PMP1 coating.

We claim:

1. An antimicrobial compound comprising
an ampetoid component,
wherein the ampetoid component comprises a trimer of a formula —(—X—Y—Z—)—$_n$, wherein X, Y, and Z are independently selected monomeric residues, wherein each monomeric residue is independently selected from proline residues and N-substituted glycine residues,
wherein the N-substituents are independently selected from about C$_4$- about C$_{20}$ linear, branched and cyclic alkyl moieties, α-amino acid side chain moieties and carbon homologs thereof,
provided the ampetoid component is amphipathic and has a net positive charge under physiological conditions,
an anchor component,
wherein the anchor component comprises at least two DOPA residues and a lysine residue,
an anti-fouling component,
wherein the anti-fouling component comprises at least one N-methoxyethylglycine (N$_{me}$) residue,
wherein the anti-fouling component couples the ampetoid component and the anchor component,
wherein the antimicrobial compound comprises a formula

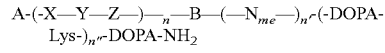

wherein A is selected from H and a terminal N-alkyl substituted glycine residue, N$_R$,
wherein R is selected from C$_4$-C$_{20}$ linear, branched and cyclic alkyl moieties,
wherein in the trimer —(—X—Y—Z—)—$_n$, X is selected from an N-(4-(aminobutyl)glycine (N$_{Lys}$) residue, at least one of Y and Z is selected from N-(phenylmethyl)glycine (N$_{pm}$), (R)—N-(1-phenylethyl)glycine (N$_{gpe}$), and (S)—N-(1-phenylethyl) glycine (N$_{spe}$) residues, and n is an integer selected from the group consisting of 1-5, wherein B is selected from a covalent bond, an $N_{Lys}$ residue and $N_{Lys}$-$N_{spe}$ residues, wherein n' is an integer selected from the group consisting of 10-25, and wherein n'' is an integer selected from the group consisting of 1-5.

2. The compound of claim 1 wherein A is H; and n is 3-4.

3. The compound of claim 2 wherein n is 3; and B is $N_{Lys}$-$N_{spe}$ residues, said ampetoid component of a formula

4. The compound of claim 2 wherein n is 4; and B is selected from a covalent bond and an $N_{Lys}$ residue, said ampetoid component of a formula

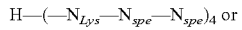

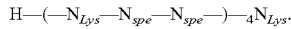

5. The compound of claim 1 wherein said ampetoid component is of a formula

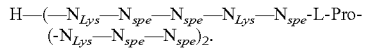

6. The compound of claim 2 wherein A is a terminal N-alkyl substituted glycine residue, said alkyl substituent R selected from about $C_6$ to about $C_{18}$ linear alkyl moieties; B is a covalent bond; and n is selected from 1 and 2.

7. The compound of claim 2 wherein A is a terminal N-alkyl substituted glycine residue, said alkyl substituent R selected from about $C_6$ to about $C_{18}$ linear, branched and cyclic alkyl moieties; B is an $N_{Lys}$ residue; and n is 1.

8. The compound of claim 7 wherein said ampetoid component is of a formula

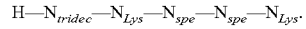

9. An article of manufacture comprising a metal substrate and a coating coupled thereto, said coating comprising an antimicrobial compound selected from compounds of claim 1.

10. The article of claim 9 wherein said anchor component comprises a (DOPA-Lys)$_2$-DOPA sequence of residues.

11. The article of claim 9 wherein said substrate is a medical device.

12. The article of claim 11 wherein said substrate comprises titanium oxide.

13. An antimicrobial compound of a formula

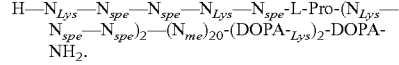

* * * * *